United States Patent
McGuigan et al.

(10) Patent No.: US 10,005,810 B2
(45) Date of Patent: Jun. 26, 2018

(54) PROCESS FOR PREPARING NUCLEOSIDE PRODRUGS

(71) Applicant: University College Cardiff Consultants Limited, Cardiff (GB)

(72) Inventors: Chirstopher McGuigan, Peterson Super Ely (GB); Fabrizio Pertusati, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 118 days.

(21) Appl. No.: 14/442,987

(22) PCT Filed: Nov. 15, 2013

(86) PCT No.: PCT/GB2013/053018
§ 371 (c)(1),
(2) Date: May 14, 2015

(87) PCT Pub. No.: WO2014/076490
PCT Pub. Date: May 22, 2014

(65) Prior Publication Data
US 2015/0291650 A1  Oct. 15, 2015

(30) Foreign Application Priority Data

Nov. 16, 2012  (GB) .................................. 1220666.0
Apr. 23, 2013  (GB) .................................. 1307314.3

(51) Int. Cl.
| | |
|---|---|
| *C07H 19/20* | (2006.01) |
| *C07H 19/173* | (2006.01) |
| *A01N 43/04* | (2006.01) |
| *A61K 31/70* | (2006.01) |
| *C07H 1/00* | (2006.01) |
| *C07H 19/06* | (2006.01) |
| *C07H 19/16* | (2006.01) |
| *B82Y 20/00* | (2011.01) |
| *B01J 27/128* | (2006.01) |
| *C07H 19/10* | (2006.01) |
| *H01S 5/343* | (2006.01) |

(52) U.S. Cl.
CPC ............ *C07H 19/20* (2013.01); *B01J 27/128* (2013.01); *B82Y 20/00* (2013.01); *C07H 1/00* (2013.01); *C07H 19/06* (2013.01); *C07H 19/10* (2013.01); *C07H 19/16* (2013.01); *H01S 5/34326* (2013.01)

(58) Field of Classification Search
CPC .......... C07H 1/00; C07H 19/06; C07H 19/16; C07H 19/20; C07H 19/10; B82Y 20/00; B01J 27/128; H01S 5/34326
See application file for complete search history.

(56) References Cited

U.S. PATENT DOCUMENTS

| | | | | |
|---|---|---|---|---|
| 7,462,605 B2 * | 12/2008 | Shepard | ........... | A61K 47/48023 514/51 |
| 7,608,599 B2 * | 10/2009 | Klumpp | ................. | C07H 19/04 514/43 |
| 7,951,787 B2 * | 5/2011 | McGuigan | ............. | C07H 19/10 514/43 |
| 8,263,575 B2 * | 9/2012 | McGuigan | ............. | C07H 19/20 514/47 |
| 8,642,756 B2 * | 2/2014 | Ross | ...................... | C07H 19/10 536/117 |
| 8,658,616 B2 * | 2/2014 | McGuigan | ............. | C07H 19/20 514/47 |
| 8,759,318 B2 * | 6/2014 | Chamberlain | ....... | C07H 19/167 514/43 |

(Continued)

FOREIGN PATENT DOCUMENTS

| | | |
|---|---|---|
| CA | 2 931 804 A1 * | 6/2015 |
| CN | 102348712 A | 2/2012 |

(Continued)

OTHER PUBLICATIONS

Furman et al., "Activity and the Metabolic Activation Pathway of the Potent and Selective Hepatitis C Virus Pronucleotide Inhibitor PSI-353661," Antiviral Research, 91(2), 120-132 (May 12, 2011—on-line publication date).*

(Continued)

*Primary Examiner* — Lawrence E Crane
(74) *Attorney, Agent, or Firm* — Foley Hoag LLP

(57) ABSTRACT

Provided are phosphoramidate nucleoside compounds of Formula (I), or pharmaceutically acceptable salts or esters or solvates thereof, useful in the treatment of cancer, viral infections and other diseases:

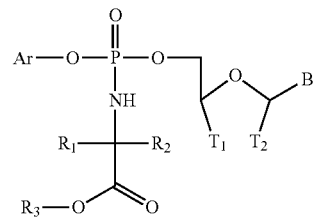

Also provided is a process for the synthesis of the compounds of Formula (I) where a desired enantiomer, having regard to the asymmetric chiral center of the phosphorus atom P, is provided in an enriched amount. The process comprises admixing a nucleoside with a phosphorochloridate in the presence of a catalyst comprising a metal salt selected from the group consisting of salts of Cu, Fe, La and Yb.

2 Claims, 8 Drawing Sheets

(56) References Cited

U.S. PATENT DOCUMENTS

| | | | |
|---|---|---|---|
| 8,871,737 B2* | 10/2014 | Smith | C07H 19/06 514/47 |
| 8,933,053 B2* | 1/2015 | McGuigan | C07F 9/6555 514/51 |
| 9,090,642 B2* | 7/2015 | Cho | C07H 1/00 |
| 9,221,866 B2* | 12/2015 | McGuigan | C07F 9/6555 |
| 9,278,990 B2* | 3/2016 | Smith | C07H 19/06 |
| 9,365,605 B2* | 6/2016 | Beigelman | A61K 31/14 |
| 9,370,528 B2* | 6/2016 | Schentag | A61K 45/06 |
| 9,487,544 B2* | 11/2016 | Cho | C07H 1/00 |
| 2003/0109697 A1 | 6/2003 | Shepard et al. | |
| 2015/0272885 A1* | 10/2015 | Ashley | A61K 45/06 424/450 |

FOREIGN PATENT DOCUMENTS

| | | |
|---|---|---|
| CN | 102459299 A | 5/2012 |
| WO | WO-2003/068164 A2 | 8/2003 |
| WO | WO-2004/041203 A2 | 5/2004 |
| WO | WO-2005/012327 A2 | 2/2005 |
| WO | WO-2010/081082 A2 | 7/2010 |
| WO | WO-2011/123672 A1 | 10/2011 |
| WO | WO-2011/0123672 A1 | 10/2011 |
| WO | WO-2012/012465 A1 | 1/2012 |
| WO | 2015/080949 A1 * | 6/2015 |

OTHER PUBLICATIONS

International Search Report from PCT/GB2013/053018, dated Dec. 20, 2013.

International Search Report and Written Opinion for Singapore Application No. 11201503750Y dated May 17, 2016.

Quintiliani, et al., "Design, synthesis, and biological evaluation of 2-deoxy-2,2-difluoro-5-halouridine phosphoramidate ProTides," Bioorg Med Chem, 19(14): 4338-4345 (2011).

Wu, et al., "Synthesis and Biological Activity of Gemcitabine Phosphoramidate Prodrug," J Med Chem, 50(15): 3743-3746 (2007).

Cho, J.-H. et al., "Efficient synthesis of nucleoside aryloxy phosphoramidate prodrugs utilizing benzylocarbonyl protection", *Tetrahedron,* 67(30):5487-5493 (USA, Jul. 1, 2011).

Cho, J.-H. et al., "Efficient Synthesis of Exo-N-carbamoyl Nucleosides: Application to the Synthesis of Phosphoramidate Prodrugs", *Organic Letters,* 14(10):2488-2491 (USA, May 18, 2012).

Chilean Search Report for Chilean Patent Application No. 14/442,897 dated Feb. 9, 2017.

* cited by examiner

PROCESS FOR PREPARING NUCLEOSIDE PRODRUGS

CROSS-REFERENCE TO RELATED APPLICATIONS

This application is the U.S. national phase of International Patent Application No. PCT/GB2013/053018, filed Nov. 15, 2013; which claims the benefit of United Kingdom Patent Application No. GB1220666.0, filed Nov. 16, 2012; and United Kingdom Patent Application No. GB1307314.3, filed Apr. 23, 2013.

The present invention relates to a process for preparing chemical compounds and to the chemical compounds prepared by the present process.

The chemical synthesis of a chiral compound usually results in a racemic mixture of the compound in which R and S enantiomers are present in equal amounts.

Many biologically active systems, however, involve specific enantiomers or diastereoisomers of chiral compounds. Such chiral biological systems may react differently to the different enantiomers or diastereoisomers of a pharmaceutical chiral compound.

Administering to a patient a racemic mixture of a chiral pharmaceutical compound may mean that only one enantiomer of the compound can partake in the desired therapeutic reaction. The synthesis of a chiral pharmaceutical compound can include additional and expensive steps performed on the racemic mixture to enrich the end product with the desired enantiomer. Such steps include, for example, chiral chromatography. In past processes, expenditure is thus necessarily incurred, either due to the preparation of a racemic mixture only a part of which is usefully pharmaceutically active or due to the additional process steps performed to remove at least some of the non-desired enantiomer from the racemic mixture prior to administration of the compound to a patient in need thereof.

A need thus exists to provide a more cost effective process for preparing a chiral compound for therapeutic use where the compound comprises at least an enriched portion of a desired enantiomer.

The present invention provides a process that meets this need.

The present invention also provides the compounds provided by the present process and pharmaceutical compositions comprising such compounds.

In particular, the present process provides a process for preparing phosphoramidates of nucleosides where a desired enantiomer, having regard to the asymmetric chiral centre of the phosphorus atom P, is provided in an enriched amount.

Throughout the present application, the R/S system of nomenclature of enantiomers is followed. A chiral centre having regard to the phosphorus atom P is labeled $R_P$ or $S_P$ according to a system in which the substituents on the atom P are each assigned a priority based on atomic number, according to the Cahn-Ingold-Prelog priority rules (CIP). Reference concerning the CIP rules is made to "Advanced Organic Chemistry" by J. March published by John Wiley & Sons (2007) and IUPAC Rules for the Nomenclature of Organic Chemistry, Section E, Stereochemistry (1974). The CIP rules allocate the lowest priority to the direct substituent on the chiral centre P having the lowest atomic number. In the case of a phosphoramidate, this substituent is N. The P centre is then orientated so that the N substituent is pointed away from the viewer. The atoms or next nearest atoms, if present, to the three O atoms directly linked to P are then considered, according to the CIP rules. If these atoms decrease in atomic number when viewed in a clockwise direction, the enantiomer is labeled $R_P$. If these atoms decrease in atomic number in a counterclockwise direction, the enantiomer is labeled $S_P$.

According to the present invention there is provided a process for the preparation of a compound of Formula I, wherein Formula I is:

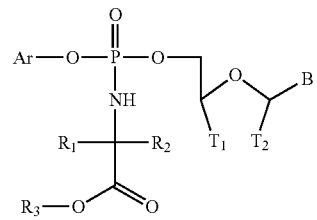

wherein:

Ar is selected from $C_{6-30}$aryl and $C_{6-30}$heteroaryl, each of which is optionally substituted;

$R_1$, $R_2$ and $R_3$ are, independently, selected from H and the group consisting of $C_{1-20}$alkyl, $C_{2-20}$alkenyl, $C_{1-20}$alkoxy, $C_{1-20}$alkoxyC$_{1-20}$alkyl, $C_{1-20}$alkoxyC$_{6-30}$aryl, $C_{2-20}$alkynyl, $C_{3-2}$-cycloalkylC$_{6-30}$aryl, $C_{6-30}$aryloxy and $C_{5-20}$heterocyclyl, any of which is optionally substituted;

$T_1$ and $T_2$ are linked together and together are selected from the group consisting of:

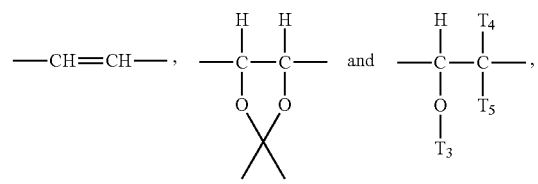

where $T_3$ is selected from the group consisting of H and —COOC$_{1-6}$alkyl and $T_4$ and $T_5$ are, independently, selected from the group consisting of H, F, Cl, Br, I, OH and methyl ($CH_3$);

and B is selected from the group consisting of a heterocyclic moiety derived from purine and a heterocyclic moiety derived from pyrimidine;

comprising the steps of:

(i) dissolving a compound of Formula II in a solvent selected from the group consisting of an ethereal solvent, acetonitrile and mixtures thereof and admixing the dissolved compound of Formula II with a base, wherein Formula II is:

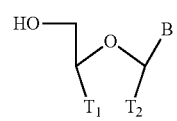

where $T_1$, $T_2$ and B have the same meanings set out with respect to Formula I;

(ii) admixing the product of step (i) with a compound of Formula III, wherein Formula III is:

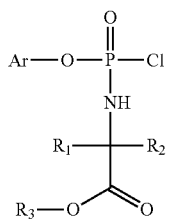

where Ar, $R_1$, $R_2$ and $R_3$ have the same meanings set out with respect to Formula I,
wherein step (ii) takes place in the presence of a catalyst comprising a metal salt selected from the group consisting of salts of Cu, Fe, La and Yb.

Suitably, an ethereal solvent is employed in step (i).

Suitably, the catalyst is admixed with the nucleoside compound of Formula II, prior to the dissolution of the compound of Formula II in the solvent of step (i).

Suitably, the phosphorochloridate of Formula III is dissolved in a solvent. The solvent is suitably selected from the group consisting of an ethereal solvent, acetonitrile and mixtures thereof. Suitably, the solvent is an ethereal solvent.

Where a solvent is employed to dissolve the phosphoramidate of Formula III, it may be the same as or different to the solvent employed to dissolve the compound of Formula II in step (i). Suitably, it is the same. Suitably, it is the same and is an ethereal solvent.

The reaction of the present process is suitably performed under an inert atmosphere, for example of argon or nitrogen.

The reaction of the present process is suitably carried out under a dry atmosphere.

The reaction of the present process is suitably carried out with stirring.

The present process can be carried out at room temperature. Room temperature is defined herein to be between 15 and 25° C.

The reaction of the present process can be monitored by HPLC (High Performance/Pressure Liquid Chromatography).

When the reaction of the present process is complete, the desired compound is separated. For example, solvent can be evaporated under reduced pressure and the residue can be purified by column chromatography.

If desired, additional steps, such as chiral column chromatography can be performed on the product of the above process to enhance yet further the $R_P:S_P$ ratio of the phosphoramidate nucleoside produced. Such additional steps can comprise standard techniques known to those skilled in the art, for example, use of a chiral HPLC column.

Where compounds produced by the present process have two or more chiral centers, they may additionally exist as diastereoisomers, which, if desired, can be separated by conventional techniques such as preparative chromatography.

Any or all of the process steps disclosed herein relating to the present invention may be employed in any combination, as desired.

Although the inventors do not wish to be bound by any theory, it is believed that the present process involves a mechanism in which the metal salt interacts with the nucleoside of Formula II such that the nucleoside is directed to react with the phosphorochloridate of Formula III in a selected diastereospecific manner. In particular, it is believed that the O ring atom in the sugar moiety of the nucleoside of Formula II is required to assist this mechanism. It is also believed, although the inventors do not wish to be bound by any theory, that this mechanism is assisted by the presence of an NH moiety, where the N is a heteroatom in an aromatic ring moiety of B and/or, where B consists of a heterocyclic moiety derived from purine, by the presence of an exocyclic heteroatom selected from the group consisting of N, O, S and Cl, preferably N, directly linked to position 2 of the aromatic ring moiety of B, for example, by the presence at position 2 of a substituent selected from $NH_2$, $NHC_{1-6}$alkyl, OH, $OC_{1-6}$alkyl, SH, $SC_{1-6}$alkyl or Cl, and is preferably $NH_2$.

By use of the present invention, mixtures of $R_P$ and $S_P$ enantiomers can be prepared in which the ratio of $R_P:S_P$ is not equal to 1.

Suitably, mixtures of phosphoramidated nucleosides can be prepared by the present process where the ratio of $R_P:S_P$ is more than 1, suitably more than 2.5, more suitably more than 5, even more suitably more than 7.5. Ideally the upper limit sought to the ratio of $R_P:S_P$ is 100:0. Practically, the upper limit to the ratio of $R_P:S_P$ available by use of the above process may be less than 100:0, but very usefully it could be as high as 20:1. If desired, additional process steps can be undertaken, for example chiral column chromatography, to enhance yet further the ratio of $R_P:S_P$ of enantiomers produced by the present process, so as to achieve, if desired, a ratio of 100:0.

Alternatively, use of the present invention may produce a mixture of phosphoramidated nucleosides where the ratio of $R_P:S_P$ is less than 1, suitably less than 2.5, more suitably less than 5, even more suitably less than 7.5. Ideally the lower limit sought to the ratio of $R_P:S_P$ is 0:100. Practically, the lower limit to the ratio of $R_P:S_P$ available by use of the above process may be more than 0:100, but very usefully it could be as low as 1:20. If desired, additional process steps can be undertaken, for example chiral chromatography, to enhance yet further the ratio of $R_P:S_P$ of enantiomers produced by the present process, so as to achieve, if desired, a ratio of 0:100.

The present process is applicable to the phosphorochloridates of Formula III. It is believed, however, that the present process is particularly suitable for use with phosphorochloridates where one or more of the moieties Ar, $R_1$, $R_2$ and $R_3$ comprise moieties that are relatively large sterically. Such phosphorochloridates are believed to interact favorably with compounds of Formula II, especially where, as mentioned above, B has an NH moiety as part of its aromatic ring system or, where B is derived from a purine moiety has, at position 2, an exocyclic heteroatom, such as a substituent comprising $NH_2$, $NHC_{1-6}$ alkyl, OH, $OC_{1-6}$ alkyl, SH, $SC_{1-6}$alkyl or Cl, preferably $NH_2$, directly linked to its aromatic ring system. Particularly preferred compounds of Formula III for use in the present process include those where Ar is naphthyl, one of $R_1$ and $R_2$ is a secondary or tertiary alkyl group and/or $R_3$ is either a tertiary alkyl group or benzyl. Particularly preferred are compounds of Formula III where, in combination, Ar is naphthyl, one of $R_1$ and $R_2$ is tertiary alkyl and $R_3$ is tertiary alkyl. Suitably, Ar can alternatively be phenyl, especially where one of $R_1$ and $R_2$ is a secondary or tertiary alkyl group, especially a tertiary alkyl group, and $R_3$ is a tertiary alkyl group or is benzyl, especially a tertiary alkyl group. Particularly preferred are compounds of Formula III where, in combination, Ar is phenyl, one of $R_1$ and $R_2$ is tertiary alkyl and $R_3$ is tertiary alkyl. Particularly preferred compounds of Formula III for use in the present process include those where Ar is naphthyl, one of $R_1$ and $R_2$ is a secondary or tertiary alkyl group and/or $R_3$ is a secondary alkyl group, a tertiary alkyl group or benzyl. Particularly preferred are compounds of Formula III where, in combination, Ar is naphthyl, one of $R_1$ and $R_2$ is tertiary alkyl and $R_3$ is tertiary alkyl. Suitably, Ar can alternatively be phenyl, especially where one of $R_1$ and $R_2$ is a secondary or tertiary alkyl group, especially a tertiary alkyl group, and $R_3$ is a secondary alkyl group, a tertiary alkyl group or is benzyl, especially a tertiary alkyl group. Particularly preferred are compounds of Formula III where, in combination, Ar is phenyl, one of $R_1$ and $R_2$ is tertiary alkyl and $R_3$ is tertiary alkyl. Alternatively, preferred compounds of Formula III have, in any combination, one of $R_1$ and $R_2$ as a primary alkyl and one of $R_1$ and $R_2$ as hydrogen, as in for example L-alaninyl or D-alaninyl, $R_3$ as a secondary alkyl group, as in for example isopropyl, a tertiary alkyl group, as in for example neopentyl, or benzyl and Ar as naphthyl or phenyl. Specific examples of preferred phosphorochloridates of Formula III include:
naphthyl(oneopentyl-L-alaninyl)phosphorochloridate;
phenyl(oneopentyl-L-alaninyl)phosphorochloridate;
naphthyl(benzyl-D-alaninyl)phosphorochloridate;
naphthyl(benzyl-L-valinyl)phosphorochloridate;
phenyl(benzyl-L-alaninyl)phosphorochloridate;
naphthyl(isopropyl-L-alaninyl)phosphorochloridate; and
phenyl(isopropyl-L-alaninyl)phosphorochloridate.

The phosphorochloridate is suitably employed in the present process in an amount that is the molar equivalent to the amount of the nucleoside of Formula II employed. In practice, if desired, the amount of phosphorochloridate employed can be in the range of from 0.5 to 1.5, more suitably in the range of from 0.75 to 1.25 of the molar equivalent amount of the nucleoside of Formula II employed. If desired, an amount of phosphorochloridate can be employed in the present process in an amount that is up to five times, preferably up to three times, the molar equivalent amount of the nucleoside of Formula II.

Where an "ethereal solvent" is employed for dissolving the phosphorochloridate, what is meant is an organic solvent that contains one or more, suitably up to and including three, more suitably up to and including two, —C—O—C moieties. Suitably, molecules of the solvent have a maximum C content of 12. Preferred examples of such solvents include: DME, which is 1,2-dimethoxyethane ($CH_3$—O—$(CH_2)_2$—O—$CH_3$); THF, which is tetrahydrofuran ($C_4H_8O$); 1,4-dioxane, which is 1,4-dioxacyclohexane ($C_4H_8O_2$); diethyl ether ($C_2H_5$—O—$C_2H_5$); diphenyl ether ($C_6H_5$—O—$C_6H_5$); anisole, which is methoxybenzene ($C_6H_5$—O—$CH_3$); and dimethoxybenzene ($C_6H_4(OCH_3)_2$). A single ethereal solvent may be used or a mixture of ethereal solvents may be used.

The catalyst to be active in the present process must be the salt of a metal. "Oxides" are excluded from the definition of "salt", as used in the present application.

Particularly preferred metal salts for use as the catalyst are copper salts, both Cu(I) and Cu(II) salts being useful in the present process, although Cu(II) salts are preferred. Particular preferred examples of copper salts that may be used in the present process include $Cu(OTf)_2$, CuCl, CuBr, CuI, $Cu(OAc)_2.H_2O$ and anhydrous $CuSO_4$. Particular preferred examples of copper salts that may be used in the present process include $Cu(OTf)_2$, CuCl, CuBr, CuI, Cu(OAc), $Cu(OAc)_2.H_2O$, anhydrous $CuSO_4$ and $Cu(OC(O)CF_3)_2$. Especially preferred is $Cu(OTf)_2$. Also especially preferred is Cu(OAc). Cu(OAc) is especially suitable where B is a heterocyclic moiety derived from pyrimidine, as, for example, present in gemcitabine.

Throughout the present application, "OTf" stands for the anion $CF_3SO_3^-$, which is the anion of trifluoromethanesulphonic acid and "OAc" stands for the anion $CH_3CO_2^-$.

Alternative catalysts that may be used in the present process are metal salts where the metal has an oxidation state of more than one and up to and including three. Especially preferred are metal salts of OTf where the metal has an oxidation state of more than one. Preferred examples of such salts include $Cu(OTf)_2$, $Yb(OTf)_3$, $Fe(OTf)_3$, and $La(OTf)_3$, with $Cu(OTf)_2$ being preferred. Other preferred metal salts suitable for use as catalysts in the present process where the metal has an oxidation state of more than one include tris(acetylacetonato)iron(III) (formula: $Fe(C_5H_7O_2)_3$) and bis(acetylacetonato)iron(II) (formula: $Fe(C_5H_7O_2)_2$).

The catalyst is suitably used in a concentration in the range of from 0.05 to 1.5 molar equivalent, more suitably in the range of from 0.05 to 1.25 molar equivalent, even more suitably in the range of from 0.05 to 0.5 molar equivalent, even more suitably in the range of from 0.075 to 0.25 molar equivalent, even more suitably at a molar equivalent amount of 0.1, relative to the molar amount of the phosphorochloridate of Formula III employed in the present process.

The metal salt of the catalyst must include one or more anions. Examples of suitable anions include $CF_3SO_3^-$, $Cl^-$, $Br^-$, $I^-$, $CH_3CO_2^-$, $SO_4^{2-}$ or $CF_3CO_2^-$. A further example of a suitable anion is the acetylacetonato anion having the formula $(O—CH(CH_3)—CH_2—CH(CH_3)—O)^-$. The metal component of the metal salt may be present either unco-ordinated, as exemplified above, or in the form of a complex where a metal cation component is co-ordinated with one or more ligands. Suitably 1, 2, 3 or 4 ligands may be bound to the metal cation component in the complex. The metal cation component in the complex is preferably a copper cation component. Examples of suitable ligands include MeCN and $C_6H_6$. Examples of suitable complexes include $(Cu(MeCN)_4)^+$ and $(CuC_6H_6)^+$. Examples of suitable metal salts that include the metal component in the form of a complex where the metal cation component is co-ordinated with one or more ligands include $Cu(MeCN)_4.CF_3SO_3$ and $Cu(C_6H_6).CF_3SO_3$.

Suitably, the metal component of the present catalyst is unco-ordinated and the metal component of the catalyst is not bound to one or more ligands. It is believed that the metal component of the present catalyst is more suitably unco-ordinated in order to act as a catalyst. Although the inventors do not wish to be bound by any theory, it is believed that metal components that are not bound to ligands can more readily interact with the O ring atom of the sugar moiety of the nucleoside and also, possibly, the NH moiety and/or the exocyclic heteroatom moiety of B, as discussed above.

Where the solvent employed in step (i) of the present process to dissolve the nucleoside of Formula II is an ethereal solvent, an organic solvent is meant that contains one or more, up to and including, suitably, three, more suitably up to and including two, C—O—C moieties. Suitably molecules of the ethereal solvent have a maximum C content of 12. Preferred examples of such solvents include: DME, which is 1,2-dimethoxyethane ($CH_3$—O—$(CH_2)_2$—O—$CH_3$); THF, which is tetrahydrofuran ($C_4H_8O$); 1,4-dioxane, which is 1,4-dioxacyclohexane ($C_4H_8O_2$); diethyl ether ($C_2H_5$—O—$C_2H_5$); anisole, which is methoxybenzene ($C_6H_5$—O—$CH_3$); and dimethoxybenzene ($C_6H_4(CH_3)_2$). A single ethereal solvent may be used or mixture of ethereal solvents may be used.

It is believed that the base employed in step (i) of the present process should preferably be selected from the group consisting of $NR_4R_5R_6$, where $R_4$, $R_5$ and $R_6$ are selected, independently, from the group consisting of $C_{1-3}$ alkyl and H, provided that at least two of $R_4$, $R_5$ and $R_6$ are, independently, $C_{1-3}$ alkyl. Suitable examples of such bases include: DIPEA, which is N,N-diisopropylethylamine ((i-Pr)$_2$NEt); (i-Pr)$_2$NH; and N(Et)$_3$. DIPEA and (i-Pr)$_2$NH are preferred. DIPEA, (i-Pr)$_2$NH and N(Et)$_3$ are preferred. Alternatively the base DBU, which is 1,8-diazabicyclo[5.4.0]undec-7-ene ($C_9H_{16}N_2$), may be employed.

The base employed in the present process is suitably present in an amount between 1 and 2 molar equivalents, more suitably in an amount between 1.25 and 1.75 molar equivalents, compared to the amount of phosphorochloridate employed. Most suitably, the base is employed in an amount of 1.5 molar equivalents of the amount of phosphorochloridate employed.

With respect to $T_1$ and $T_2$ in Formulae I and II, $T_1$ and $T_2$ suitably comprise $T_3$, $T_4$ and $T_5$, as set out above, and, more suitably, comprise $T_4$ being the same as $T_5$, for example, $T_4$ and $T_5$ can both be F or H, or alternatively, more suitably, $T_4$ and $T_5$ are not the same, for example, $T_4$ is $CH_3$ or H and $T_5$ is OH or F, particularly preferred examples being $T_4$ as $CH_3$ in combination with $T_5$ as OH, $T_4$ as H in combination with $T_5$ as F and $T_4$ as H in combination with $T_5$ as OH. Suitably, if present, only one of $T_4$ and $T_5$ is OH. Suitably, $T_3$ is H or $CO_2tBu$, especially in combination with any of the immediately preceding combinations disclosed for $T_4$ and $T_5$. Particularly preferred combinations of $T_3$, $T_4$ and $T_5$ include: $T_3$ as H, $T_4$ as $CH_3$ and $T_5$ as OH; $T_3$ as H, $T_4$ as H and $T_5$ as H; $T_3$ as H, $T_4$ as H and $T_5$ as F; $T_3$ as H, $T_4$ as H and $T_5$ as OH; $T_3$ as H, $T_4$ as OH and $T_5$ as H; and $T_3$ as $CO_2tBu$, $T_4$ as F and $T_5$ as F. Suitably, together $T_3$ is not H, each of $T_4$ and $T_5$ is not F and B is not 4-amino-pyrimidine-2(1H)-one where the N1 atom of the pyrimidine derived moiety is linked directly with the C1 atom of the sugar moiety. Suitably, together $T_3$ is not H, each of $T_4$ and $T_5$ is not F and B is not 4-amino-pyrimidine-2(1H)-one where the N1 atom of the pyrimidine derived moiety is linked directly with the C1 atom of the sugar moiety, in combination with the catalyst being Cu(OTf)$_2$ or any of Cu(OTf)$_2$, Yb(OTf)$_3$, Fe(OTf)$_3$ and La(OTf)$_3$.

The present process can be employed to prepare a compound of Formula I where B is derived from a purine moiety or a pyrimidine moiety.

Where B is derived from a purine moiety, suitably B of the nucleoside moiety of the compound of Formula II is as follows, where the N atom marked with * links directly to the C1 atom of the sugar moiety:

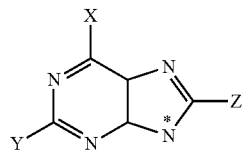

where each of X and Z is, independently, selected from H, OH, F, Cl, Br, I, $OC_{1-6}$alkyl, $C_{1-6}$alkyl and $NR_7R_8$, where each of $R_7$ and $R_8$ is, independently, selected from H and $C_{1-6}$alkyl; and Y is selected from H, OH, $OC_{1-6}$alkyl, SH, $SC_{1-6}$alkyl, F, Cl, Br, I, $C_{1-6}$alkyl, $C_{2-8}$alkynyl, $NR_9R_{10}$ where each of $R_9$ and $R_{10}$ is, independently, selected from H and $C_{1-6}$ alkyl. More suitably, in combination, X is selected from $OCH_3$, $NH_2$, NH(cyclic$C_3H_5$), H, OH, F, Cl; Y is selected from H, $NH_2$, OH, F, Cl and $C_{2-8}$alkynyl; and Z is H. Preferred compounds of Formula II include those where B is derived from purine and: X is $OCH_3$, Y is $NH_2$ and Z is H; X is $NH_2$, Y is H and Z is H; X is NH(cyclic$C_3H_5$), Y is $NH_2$ and Z is H; X is $NH_2$, Y is Cl and Z is H; X is Cl, Y is $NH_2$ and Z is H; X is $NH_2$, Y is F and Z is H; and X is $NH_2$, Y is $C_{2-8}$alkynyl, preferably $C_{2-6}$alkynyl, and Z is H. Where Y is $C_{2-8}$alkynyl, preferably Y is linear $C_{2-6}$alkynyl and preferably Y contains one triple C≡C bond at the alpha position.

Where B is derived from a pyrimidine moiety, suitably B of the nucleoside moiety of the compound of Formula II is as follows, where the N atom marked with * links directly with the C1 atom of the sugar moiety:

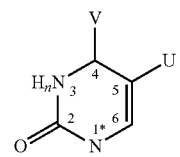

where U is selected from the group consisting of H, $C_{1-6}$alkyl, F, Cl, Br and I; and n is 0 or 1, wherein when n is 0, V is —$NH_2$ and a double bond exists between position 3 and position 4, and when n is 1, V is =O. Preferred compounds of Formula II include those where B is derived from pyrimidine and have in combination: U as H and V as $NH_2$; U as F and V as =O; and U as $CH_3$ and V as =O.

Compounds of Formula II particularly suitable for use in the present process can comprise compounds that have the preferred respective options for B derived from a purine moiety or from a pyrimidine moiety, as set out above, in combination with any of the preferred options for $T_1$ and $T_2$, as set out above.

Specific examples of compounds of Formula II suitable for use in the present process include, where the common name is given first, followed, in brackets, by the IUPAC name the following nucleosides:

2'CMe6OMeG (2-(2-amino-6-methoxy-9H-purin-9-yl)-5-(hydroxymethyl)-3-methyloxolane-3,4-diol);

nelarabine (2R,3S,4R,5R-2-(2-amino-6-methoxy-purin-9-yl)-5-(hydroxymethyl)oxolane-3,4-diol);

2',3'iPrA (2',3'-isopropylidene adenosine);

gemcitabine (4-amino-1-(2-deoxy-2,2-difluoro-β-D-erythro-pentofuranosyl)pyrimidin-2(1H)-one);

3'-boc gemcitabine (4-amino-1-(2-deoxy-2,2-difluoro-3'-tert-butoxycarbonyl-β-D-erythro-pentofuranosyl)pyrimidin-2(1H)-one));

FUDR (5-Fluoro-1-[4-hydroxy-5-(hydroxymethyl)tetrahydrofuran-2-yl]-1H-pyrimidine-2,4-dione);

d4T (1-((2R,5S)-5-(hydroxymethyl)-2,5-dihydrofuran-2-yl)-5-methylpyrimidine-2,4(1H,3H)-dione);

cladribine (5-(6-amino-2-chloro-purin-9-yl)-2-(hydroxymethyl)oxolan-3-ol);

isocladribine (2-amino-6-chloro-2'-deoxyguanosine);

fludarabine ([(2R,3R,4S,5R)-5-(6-amino-2-fluoro-purin-9-yl)-3,4-dihydroxy-oxolan-2-yl]methoxyphosphonic acid);

clofarabine (5-(6-amino-2-chloro-purin-9-yl)-4-fluoro-2-(hydroxymethyl)oxolan-3-ol);

fluorodeoxyuridine (2'-fluoro-2'-deoxyuridine);

cytarabine (4-amino-1-[(2R,3S,4R,5R)-3,4-dihydroxy-5-(hydroxymethyl)oxolan-2-yl]pyrimidin-2-one);

cytidine (4-amino-1-[3,4-dihydroxy-5-(hydroxymethyl)tetrahydrofuran-2-yl]pyrimidin-2-one); and 2'-deoxy-2'-fluoro-2-Cmethylcytidine(4-amino-1-((2R,3R,4R,5R)-3-fluoro-4-hydroxy-5-(hydroxymethyl)-3-methyltetrahydrofuran-2-yl)pyrimidin-2(1H)-one).

Preferably $R_1$ and $R_2$ are selected such that they correspond to the side chains of a natural amino acid.

Preferably one of $R_1$ and $R_2$ is Me and one of $R_1$ and $R_2$ is H, such that the C atom bearing $R_1$ and $R_2$ has chirality L as in natural alanine.

Preferably $R_3$ is alkyl, more preferably $R_3$ is selected from the group consisting of methyl, ethyl, 2-propyl, 2-butyl, —$CH_2$—$C(CH_3)_3$ and benzyl, even more preferably $R_3$ is selected from the group consisting of methyl (—$CH_3$) and benzyl (—$CH_2C_6H_5$).

By "$C_{6-30}$heteroaryl" for Ar is meant a six to thirty membered aromatic ring system that can contain one or more heteroatoms in the ring system, as further defined below.

Preferred Ar entities include phenyl, pyridyl, naphthyl and quinolyl, each of which may be substituted or unsubstituted. Especially preferred as Ar is naphthyl, particularly unsubstituted naphthyl. Pyridyl is —$C_5NH_4$.

Each of Ar, $R_1$, $R_2$ and $R_3$ can be substituted with one, two, three, four, five or more substituents independently selected from the group comprising electron donating and electron withdrawing moieties.

Substituents on Ar can be located ortho-, meta-, para- or otherwise on the aromatic groups. Substituents on Ar are suitably, independently, selected from the group consisting of hydroxy, acyl, acyloxy, nitro, amino, carboxyl, $C_{1-6}$esters, $C_{1-6}$aldehyde, cyano, $C_{1-6}$alkylamino, $C_{1-6}$dialkylamino, thiol, chloro, bromo, fluoro, iodo, $C_{1-6}$alkyl, $C_{2-6}$alkenyl, $C_{1-6}$alkoxy-$C_{1-6}$alkyl, $C_{1-6}$alkoxy-$C_{5-10}$aryl, $C_{5-7}$cycloalkyl, $C_{5-11}$cycloalkyl-$C_{1-6}$alkyl, $C_{5-7}$cycloalkenyl, $C_{5-7}$cycloalkynyl, $C_{5-11}$aryl$C_{1-6}$alkyl, $C_{1-6}$alkyl$C_{5-11}$aryl, $C_{5-11}$aryl, $C_{1-6}$fluoroalkyl, $C_{2-6}$fluoroalkenyl, $SO_3H$, SH and SR' wherein R' is independently selected from the same group as set out herein for $R_1$. Each substituent can be substituted by any other substituent. Preferred substituents on Ar are F, Cl, $CF_3$ and $NO_2$. Where Ar is phenyl, the preferred position for a single substituent, which is preferably F, Cl, $CF_3$ or $NO_2$, is para-.

Substituents on $R_1$, $R_2$ and $R_3$ are, independently, selected from the group consisting of hydroxy, acyl, acyloxy, nitro, amino, amido, carboxy, $C_{1-6}$esters, $C_{1-6}$aldehyde, cyano, $C_{1-6}$alkylamino, $C_{1-6}$dialkylamino, thiol, chloro, bromo, fluoro, iodo, $C_{5-7}$cycloalkyl, $C_{5-7}$ cycloalkenyl, $C_{5-7}$cycloalkynyl, $C_{5-11}$aryl, $C_{5-11}$aryl$C_{1-6}$alkyl, $C_{5-20}$heterocyclyl, $SO_3H$, SH and SR' wherein R' is independently selected from the same group set out herein for $R_1$. Each substituent can be substituted by any other substituent.

$R_1$ and $R_2$ are suitably independently selected from the group consisting of H, $C_{1-10}$alkyl, $C_{2-10}$alkenyl, $C_{2-10}$alkoxyl$C_{1-10}$alkyl, $C_{1-10}$alkoxy$C_{6-10}$aryl, $C_{2-10}$alkynyl, $C_{3-20}$cycloalkyl, $C_{3-20}$cycloalkenyl, $C_{4-20}$cycloalkynyl, and $C_{5-10}$heterocyclyl.

$R_1$ and/or $R_2$ are preferably a side chain of a natural amino acid selected from the group consisting of glycine, alanine, valine, leucine, isoleucine, phenylalanine, tyrosine, tryptophan, serine, threonine, lysine, arginine, histidine, aspartic acid, glutamic acid, asparagines, glutamine, cysteine and methionine. Specifically, $R_1$ and/or $R_2$ are preferably selected from the group consisting of H, $CH_3$, —$CH(CH_3)_2$, —$CH_2CH(CH_3)_2$, —$CH(CH_3)(CH_2CH_3)$, —$CH_2Ph$, —$CH_2Ph$-OH, —$CH_2SH$, —$CH_2CH_2SCH_3$, —$CH_2OH$, —$CH(CH_3)(OH)$, —$CH_2CH_2CH_2CH_2NH_3^+$, —$CH_2CH_2CH_2NHC(=NH_2^+)NH_2$, —$CH_2C(O)O—$, —$CH_2CH_2C(O)O—$, —$CH_2C(O)NH_2$, —$CH_2CH_2C(O)NH_2$,

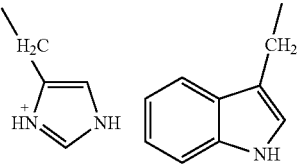

Preferably, the stereochemistry at the asymmetric centre —$CR_1R_2$ corresponds to an L-amino acid. The stereochemistry at the asymmetric centre —$CR_1R_2$ can, however, correspond to a D-amino acid. Alternatively, mixtures of compounds can be employed having asymmetric centres corresponding to L and D amino acids.

The present invention is not, however, limited to compounds having a moiety corresponding to a naturally occurring amino acid. The present invention specifically includes compounds having a moiety which corresponds to a non-naturally occurring amino acid, such as, for example, those where $R_1=R_2$=alkyl, or, where together with the C atom to which they are attached, $R_1$ and $R_2$ provide a cyclic moiety. Preferably with respect to the compound of formula I, the moiety $R_3OCOCR_1R_2NH$— corresponds to or is derived from a non-naturally occurring amino acid.

$R_3$ is suitably selected from the group consisting of H, $C_{1-10}$alkyl, $C_{2-10}$alkenyl, $C_{1-10}$alkoxy, $C_{1-10}$alkoxy$C_{1-10}$aryl, $C_{1-10}$alkoxy$C_{6-10}$aryl, $C_{2-10}$alkynyl, $C_{3-20}$cycloalkyl, $C_{3-20}$cycloalkenyl, $C_{4-20}$cycloalkynyl, and $C_{5-20}$heterocyclyl.

$R_3$ is more suitably selected from the group consisting of H, $C_{1-10}$alkyl, $C_{3-20}$cycloalkyl and benzyl.

All possible combinations for the preferred options for each of Ar, $R_1$, $R_2$, $R_3$, $T_1$, $T_2$, $T_3$, $T_4$, $T_5$ and B are herein disclosed, as are all such combinations together with all the preferred options set out herein for the process steps for performing the present process.

As used herein, the term "alkyl" refers to a straight or branched saturated monovalent cyclic or acyclic hydrocarbon radical, having the number of carbon atoms as indicated (or where not indicated, an acyclic alkyl group preferably has 1-20, more preferably 1-6, more preferably 1-4 carbon atoms and a cyclic alkyl group preferably has 3-20, preferably 3-10, more preferably 3-7 carbon atoms), optionally substituted with one, two, three or more substituents independently selected from the group set out above with respect to substituents that may be present on $R_1$, $R_2$ and $R_3$. By way of non-limiting examples, suitable alkyl groups include methyl, ethyl, propyl, butyl, pentyl, hexyl, octyl, nonyl and dodecyl. Especially preferred are tertiary alkyl radicals, including t-butyl and —$CH_2$—$C(CH_3)_3$.

As used herein, the term "alkenyl" refers to a straight or branched unsaturated monovalent acyclic or cyclic hydrocarbon radical having one or more C=C double bonds and having the number of carbon atoms as indicated (or where not indicated, an acyclic alkenyl group preferably has 2-20, more preferably 2-6, more preferably 2-4 carbon atoms and a cyclic alkenyl group preferably has 4-20, more preferably 4-6 carbon atoms), optionally substituted with one, two, three or more substituents, independently, selected from the group set out above with respect to substituents that may be present on $R_1$, $R_2$ and $R_3$. By way of non-limiting examples, suitable alkenyl groups include vinyl, propenyl, butenyl, pentenyl and hexenyl.

As used herein, the term "alkynyl" refers to a straight or branched unsaturated monovalent acyclic or cyclic hydrocarbon radical having one or more triple C≡C bonds and having the number of carbon atoms as indicated (or where not indicated, an acyclic alkynyl group preferably has 2-20, more preferably 2-6, more preferably 2-4 carbon atoms and a cyclic alkynyl group preferably has 7-20, more preferably 8-20 carbon atoms), optionally substituted with one, two, three or more substituents, independently, selected from the group set out above with respect to substituents that may be present on $R_1$, $R_2$ and $R_3$.

As use herein, the term "alkoxy" refers to the group alkyl-O—, where alkyl is as defined herein and where the alkyl moiety may optionally be substituted by one, two, three or more substituents as set out above for alkyl. By way of non-limiting examples, suitable alkoxy groups include methoxy, ethoxy, n-propoxy, iso-propoxy, n-butoxy, tert-butoxy, sec-butoxy, n-pentoxy, n-hexoxy and 1,2-dimethylbutoxy.

As used herein, the term "aryloxy" refers to the group aryl-O—, where aryl is as defined herein and where the aryl moiety may optionally be substituted by one, two, three or more substituents as set out above with respect to the group Ar.

As used herein, the term "alkoxyalkyl" refers to an alkyl group having an alkoxy substituent. Binding is through the alkyl group. The alkyl moiety and the alkoxy moiety are as defined herein with respect to the definitions of alkyl and alkoxy, respectively. The alkoxy and alkyl moieties may each be substituted by one, two, three or more substituents as set out above with regard to the definition of alkyl.

As used herein, the term "alkoxyaryl" refers to an aryl group having an alkoxy substituent. Binding is through the aryl group. The alkoxy moiety and the aryl moiety are as defined herein with respect to the definitions of alkoxy and aryl, respectively. The alkoxy and aryl moieties may each be substituted by one, two, three or more substituents, as defined herein with regard to the definitions of alkoxy and aryl, respectively.

As used herein, the term "cycloalkylaryl" refers to an aryl group having a cyclic alkyl substituent. Binding is through the aryl group. The cycloalkyl moiety and the aryl moiety are as defined herein with respect to the definitions of cycloalkyl and aryl, respectively. The cycloalkyl moiety and the aryl moiety may each be optionally substituted by one, two, three or more substituents as set out herein with regard to the definitions of alkyl and aryl, respectively.

As used herein, the term "aryl" refers to a monovalent unsaturated aromatic carbocyclic radical having one, two, three, four, five or six rings, preferably one, two or three rings, which may be fused or bicyclic. An aryl group may optionally be substituted by one, two, three or more substituents as set out above with respect to optional substituents that may be present on the group Ar. Preferred aryl groups are: an aromatic monocyclic ring containing 6 carbon atoms; an aromatic bicyclic or fused ring system containing 7, 8, 9 or 10 carbon atoms; or an aromatic tricyclic ring system containing 10, 11, 12, 13 or 14 carbon atoms. Non-limiting examples of aryl include phenyl and naphthyl. Preferred substituent groups are independently selected from hydroxy, acyl, acyloxy, nitro, amino, carboxyl, cyano, $C_{1-6}$alkylamino, $C_{1-6}$dialkylamino, thiol, chloro, bromo, fluoro, iodo, $SO_3H$, SH, SR' wherein R' is independently selected from the same groups as $R_1$.

As used herein, the term "$C_{6-30}$heteroaryl" refers to a monovalent unsaturated aromatic heterocyclic 6 to 30 membered radical having one, two, three, four, five or six aromatic rings, preferably one, two or three aromatic rings, which may be fused or bicyclic, and having contained within the aromatic ring at least one and up to six, suitably up to three, heteroatoms, independently, selected from the group consisting of N, O and S. Available carbon atoms and/or heteroatoms in the heteroaryl ring system may be substituted on the ring with one or more substituents as set out above with respect to the substituents that may be present on the group Ar. Preferred heteroaryl groups are: an aromatic monocyclic ring system containing six members of which at least one member is a N, O or S atom and which optionally contains one, two or three additional N atoms; an aromatic monocyclic ring having six members of which one, two or three members are a N atom; an aromatic bicyclic or fused ring having nine members of which at least one member is a N, O or S atom and which optionally contains one, two or three additional N atoms; or an aromatic bicyclic ring having ten members of which one, two or three members are a N atom. Examples include, and are not limited to, pyridyl and quinolyl.

As used herein, the term "heterocyclyl" refers to a saturated or partially unsaturated heterocyclic ring system having one, two, three, four, five or six rings, preferably one, two or three rings, which may be fused or bicyclic, and having contained within the ring or rings at least one and up to six, suitably up to three, members selected, independently, from the group consisting of N, O and S. The prefix "$C_{5-20}$" or "$C_{5-10}$" used before heterocyclyl means, respectively, a five to twenty or a five to ten membered ring system at least one of which members is selected from the group consisting of N, O and S. Preferred heterocyclyl systems are: a monocyclic ring system having five members of which at least one member is a N, O or S atom and which optionally contains one additional O atom or one, two or three additional N atoms; a monocyclic ring having six members of which one, two or three members are a N atom; a bicyclic ring system having nine members of which at least one member is a N, O or S atom and which optionally contains one, two or three additional N atoms; or a bicyclic ring system having ten members of which one, two or three members are a N atom. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

Available carbon atoms and/or heteroatoms of the "heterocyclyl" ring systems described above may be substituted on the ring with one or more heteroatoms. Where the ring(s) is substituted with one or more heteroatoms, heteroatom substituents are selected from oxygen, nitrogen, sulphur and halogen (F, Cl, Br and I). Where the ring(s) is substituted with one or more heteroatoms, preferably there are 1, 2, 3 or 4 heteroatom substituents selected from the group consisting of oxygen, nitrogen and/or halogen. Preferred substituent groups are, independently, selected from hydroxy, acyl, acyloxy, nitro, amino, carboxyl, cyano, $C_{1-6}$alkylamino, $C_{1-6}$dialkylamino, thiol, chloro, bromo, fluoro, iodo, $SO_3H$, SH and SR' wherein R' is, independently, selected from the same groups as $R_1$.

Compounds prepared by the process of the present invention may be useful the therapeutic treatment of *homo sapiens* and animals, preferably *homo sapiens*, in the treatment of cancer, including the treatment of solid cancers such as breast, colon or prostate cancer and the treatment of leukaemia, which is a malignancy of blood, and as anti-viral agents with respect to e.g. HIV, HBV, HCV and CMV. A particular example of a compound that can usefully be prepared by the process of the present invention is 2-amino-6-methoxy-9-(2'-C-methyl-β-D-ribofuranosyl)purine 5'-O-[α-naphthyl-(2,2-dimethylpropoxy-L-ananinyl)]phosphate, which is useful in the treatment of HCV.

Further specific examples of compounds of Formula I that can be suitably be prepared by the process of the present invention include phosphoramidated nucleosides prepared from compounds of Formula III which are any of the specific examples of the preferred phosphorochloridates listed above, in combination with compounds of Formula II which are any of the specific examples of the preferred nucleosides listed above. Particular, examples of such compounds are the phosphoramidated nucleosides corresponding to the products of Examples 1 to 4, 6, 7, 10 to 14, 16 to 21, 23, 26 to 27, 29 to 37, 39 to 42 and 44 to 46 below, either in the respective $R_P:S_P$ ratios illustrated in the Examples below and in ratios of $R_P:S_P$ obtained by variants of the exemplified processes that comply with the process of the present invention. An additional particular example of such compounds is isopropyl(2S)-2-[[[(2R,3R,4R,5R)-5-(2,4-dioxopyrimidin-1-yl)-4-fluoro-3-hydroxy-4-methyl-tetrahydrofuran-2-yl]methoxy-phenoxy-phosphoryl]amino]propanate.

A compound produced by the present process, or pharmaceutically acceptable salt or ester or solvate of said compound, can be used to preparing pharmaceutical compositions by combining the compound, or salt or ester or solvate thereof, with one or more pharmaceutical acceptable excipients, diluents or carriers.

For use in medicine, the salts of the compounds of this invention refer to non-toxic "pharmaceutically acceptable salts." FDA approved pharmaceutical acceptable salt forms (Ref. International J. Pharm. 1986, 33, 201-217; J. Pharm. Sci., 1977, January, 66 (1)) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, tosylate and triethiodide.

Pharmaceutically acceptable basic/cationic salts include, and are not limited to aluminum, benzathine, calcium, chloroprocaine, choline, diethanolamine, ethylenediamine, lithium, magnesium, potassium, procaine, sodium and zinc.

Pharmaceutically acceptable ester derivatives in which one or more free hydroxy groups are esterified in the form of a pharmaceutically acceptable ester are particularly prodrug esters that may be convertible by solvolysis under physiological conditions to the compounds of the present invention having free hydroxy groups.

Pharmaceutical compositions incorporating compounds produced by the present process, or salts, esters or solvates thereof, may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

The compound having formula I or a pharmaceutical composition comprising a compound having formula I according to the present invention can be administered to a patient, which may be *homo sapiens* or animal, by any suitable means. Such medicaments can be administered by oral or parenteral routes, including intravenous, intramuscular, intraperitoneal, subcutaneous, transdermal, airway (aerosol), rectal, vaginal and topical (including buccal and sublingual) administration.

For oral administration, the pharmaceutical compositions will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day. A preferred lower dose is 0.5 mg per kilogram body weight of recipient per day, a more preferred lower dose is 1 mg per kilogram body weight of recipient per day. A suitable dose is preferably in the range of 1 to 50 mg per kilogram body weight per day, and more preferably in the range of 1 to 10 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

BRIEF DESCRIPTION OF THE FIGURES

The present invention will now be described by way of example only with reference to the following examples and the following figures, wherein.

The following example sets out the experimental procedure that was employed in each of the Examples for which data are set out below.

EXPERIMENTAL PROCEDURE

Example

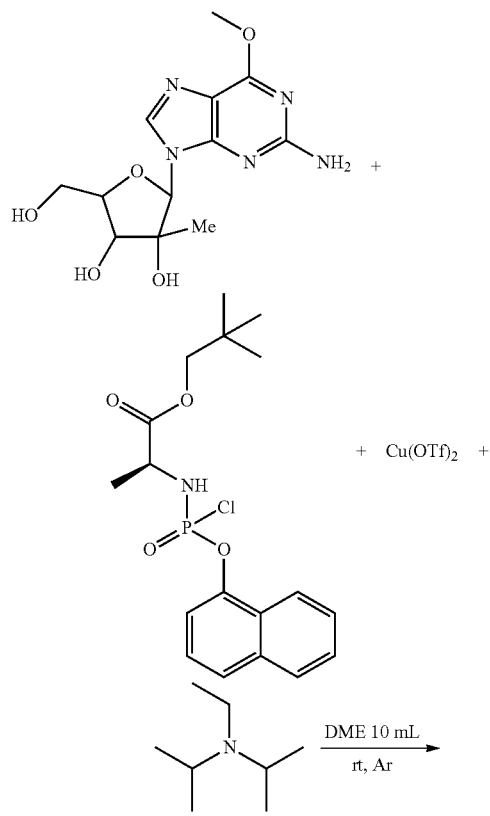

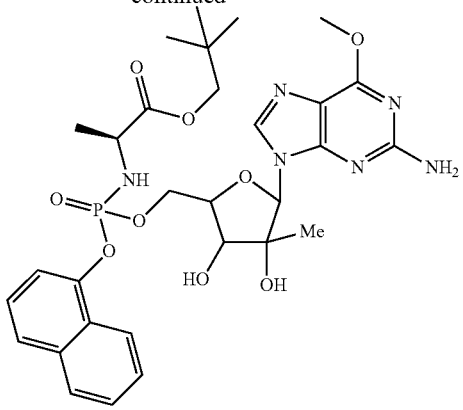

A dry round bottomed flask is charged with a magnetic stirring bar, 2'-C methyl-6-O-methylguanosine (2'CMe6OMeG) (106.0 mg, 0.34 mmol.) and catalytic amount of copper (II) trifluoromethane sulfonate (12.32 mg, 0.34 mmol., 0.1 equiv.). The flask is sealed with a rubber septum and purged with dry argon. Anhydrous 1,2-dimethoxyethane (DME, 10 mL) is added via syringe and the resulting light blue solution is stirred at room temperature for 5-10 minutes. In a separate vial, a solution of naphthyl (Oneopentyl-L-alaninyl) phosphorochloridate (131 mg, 0.34 mmol., 1 equiv.) in 2-3 mL of anhydrous THF is prepared. To the nucleoside solution is then added N,N-diisopropylethylamine (DIPEA) (62.3 mg, 0.48 mmol., 84.0 µL, 1.5 equiv.) followed by the dropwise addition of the phosphorochloridate solution previously prepared. Upon addition of the base, the solution turned from light blue to dark green and a white precipitate appeared. Addition of the phosphorochloridate solution causes the disappearance of the precipitate and the color of the solution to turn to dark blue. The mixture is then stirred at room temperature for 12 hours. The reaction is monitored by HPLC, according to the following protocol:

a 0.1-0.2 mL aliquot of solution is withdraw from the flask, under argon, via syringe and diluted with HPLC grade methanol, filtered and further diluted with a mixture of acetonitrile/water 10:90. The resulting solution is then injected into HPLC and analyzed (Reverse-phase C-18 column, eluting with $H_2O$/MeCN from 90/10 to 0/100 in 30 min, Flow=1 mL/min, $\lambda$=254 nm and $\lambda$=280 nm). A 38% yield and 1:8 Sp to Rp diastereomeric ratio are estimated by integration of the product and starting material peaks.

Figure 1:
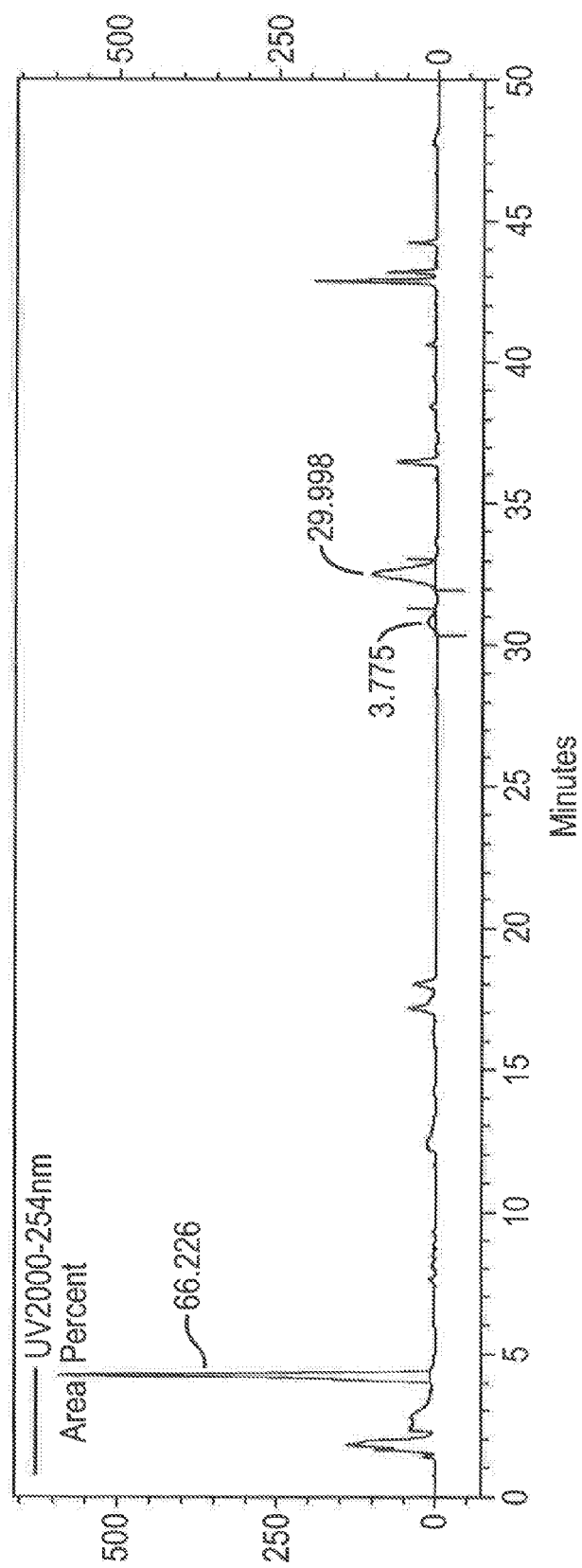
FIG. 1 shows the HPLC spectrum of the product of Example 1.

When the reaction is completed, the solvent is evaporated under reduced pressure, and the residue is purified by column chromatography on silica gel with gradient elution DCM: MeOH 98:2 to 94:6. The residue from the column is taken up in dichloromethane and washed with 0.5 M HCl (3×10 mL). The organic layer is separated, dried over sodium sulfate, filtered and evaporated to give the title compound as white solid (isolated yield: 40 mg, 20%). The isomer ratio obtained was 1:5 in favor of the $R_p$ isomer as judged from the HPLC of the pure compound, as shown in FIG. 1.

The procedure outlined above was followed in the following examples.

Examples 1 to 5

The above procedure was followed employing 2'CMe6OMeG, as set out above, as the nucleoside and each of the phosphorochloridates whose structures are set out immediately below, arranged in order of Example 1 to Example 5, and the following experimental conditions: Nucleoside. 100 mg, phosphorochloridate 1 equiv., Cu(OTf)$_2$ 0.1 equiv., DIPEA 1.5 equiv., DME 10 mL, room temperature, 12-18 hours. Example 5 is a reference example.

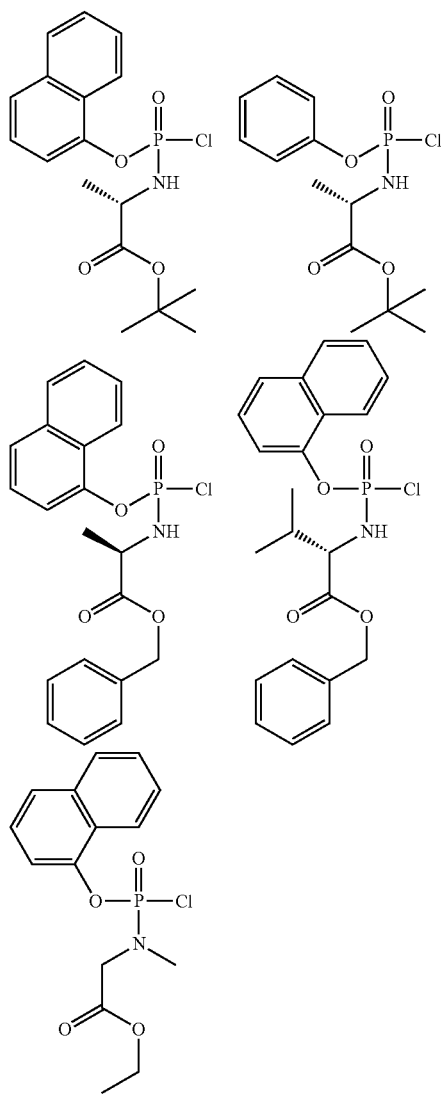

The results of the preparative processes in terms of the R$_P$:S$_P$ ratio of enantiomers isolated and the HPLC yield achieved are given in Table 1 below. "2'CMeG" in Table 1 stands for "2'CMe6OMeG", as set out above.

TABLE 1

| Variation of the phosphorochloridate | | | | |
|---|---|---|---|---|
| Example | Nucleoside | Phosphorochloridate | Ratio | Yield |
| 1 | 2'CMeG | L-Ala neopentyl, naphthyl | 1:8 | 38% |
| 2 | 2'CMeG | L-Ala neopentyl, phenyl | 1:3 | 32% |
| 3 | 2'CMeG | D-Ala benzyl, naphthyl | 1:1.1 | 8% |
| 4 | 2'CMeG | L-Val benzyl, naphthyl | 1:7.5 | 41% |
| 5 | 2'CMeG | Sarcosine ethyl, naphthyl | — | trace |

Examples 6 to 12

Following the experimental procedure set out above, one equivalent of naphthyl (Oneopentyl-L-alaninyl)phosphorochloridate was reacted with a range of nucleosides under the following conditions: Nucleoside 100 mg, phosphorochloridate 1 equiv., Cu(OTf)$_2$ 0.1 equiv., DIPEA 1.5 equiv., DME 10 mL, Room Temperature, 12-18 hours. Example 8 is a reference example.

The structure of naphthyl(Oneopentyl-L-alaninyl)phosphorochloridate and the structures of the nucleosides, arranged in order of Example 6 to Example 12, are given below:

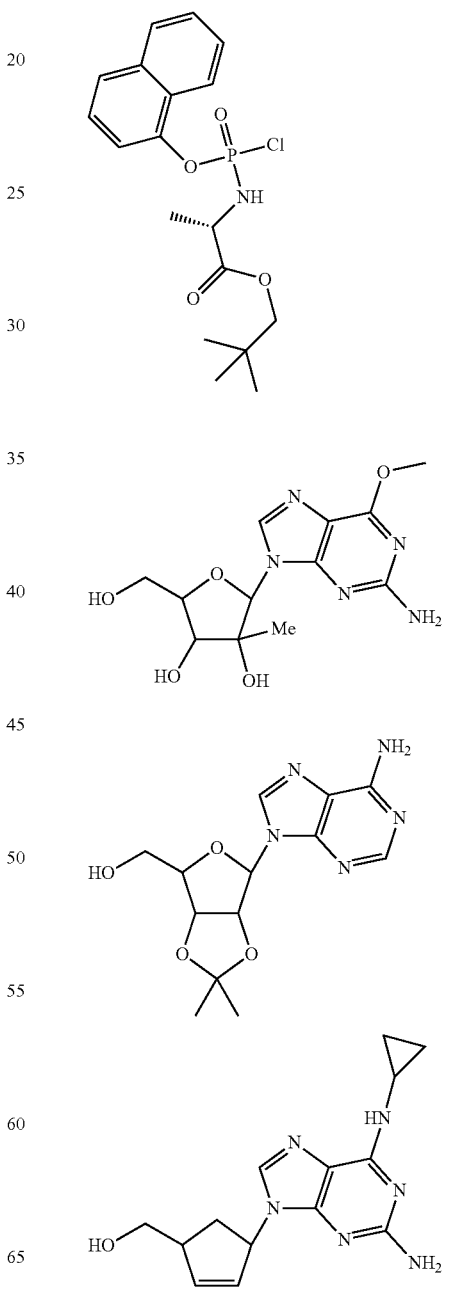

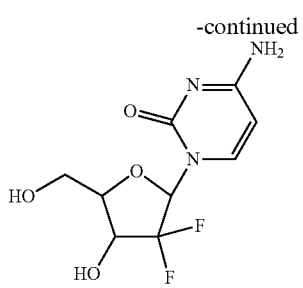

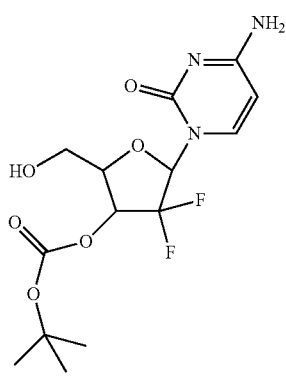

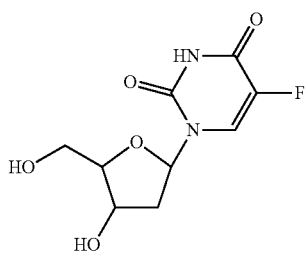

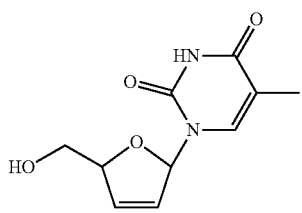

The results in terms of the ratio of $R_P:S_P$ and yield achieved are given in Table 2 below.

TABLE 2

| | Nucleoside variation | | | |
|---|---|---|---|---|
| Example | Nucleoside | Phosphorochloridate | Ratio | Yield |
| 6 | 2'CMeG | L-Ala neopentyl, naphthyl | 1:8 | 38% |
| 7 | 2',3'iPr A | L-Ala neopentyl, naphthyl | 1:1.1 | 12% |
| 8 | Abacavir | L-Ala neopentyl, naphthyl | — | — |
| 9 | Gemcitabine | L-Ala neopentyl, naphthyl | 1:1 | Trace |
| 10 | Boc Gemcitabine | L-Ala neopentyl, naphthyl | 1:2.2 | 5% |
| 11 | FUDR | L-Ala neopentyl, naphthyl | 1:2.5 | 30% |
| 12 | d4t | L-Ala neopentyl, naphthyl | 1:1.8 | 50% |

Examples 13 to 14

Copper Catalyst

Following the experimental procedure set out above and the following experimental conditions: Nucleoside 100 mg, phosphorochloridate 1 equiv., Cu(X)$_Y$ 0.1 equiv., NEt$_3$ 1.5 equiv., THF 20 mL, Room Temperature, 12-18 hours, other copper salts in place of Cu(OTf)$_2$ were tested as the catalyst. The copper salts employed and the results in terms of the ratio $R_P:S_P$ of enantiomers and the yield achieved are given in the Table 3 below.

TABLE 3

| | Screening of copper salts | | |
|---|---|---|---|
| Example | Cu salt (equiv.) | Ratio (HPLC) | (HPLC yield) |
| 13 | Cu(OAc)$_2$•H$_2$O (0.1) | 1:2.1 | (34%) |
| 14 | CuI (0.1) | 1:3.2 | (22%) |

Examples 15 to 18

Using the experimental procedure set out above, 2'CMe6OMeG as the nucleoside, naphthyl(oneopentyl-L-alaninyl)phosphorochloridate as the phosphorochloridate and the following experimental conditions: Nucleoside 100 mg, phosphorochloridate 1 equiv., Me(OTf)$_Y$ 0.1 equiv., NEt$_3$ 1.5 equiv., THF 20 mL, room temperature, N$_2$ atmosphere, 12-18 hours, metal triflates other than copper triflate were screened. The reaction is set out below. Example 15 is a reference example.

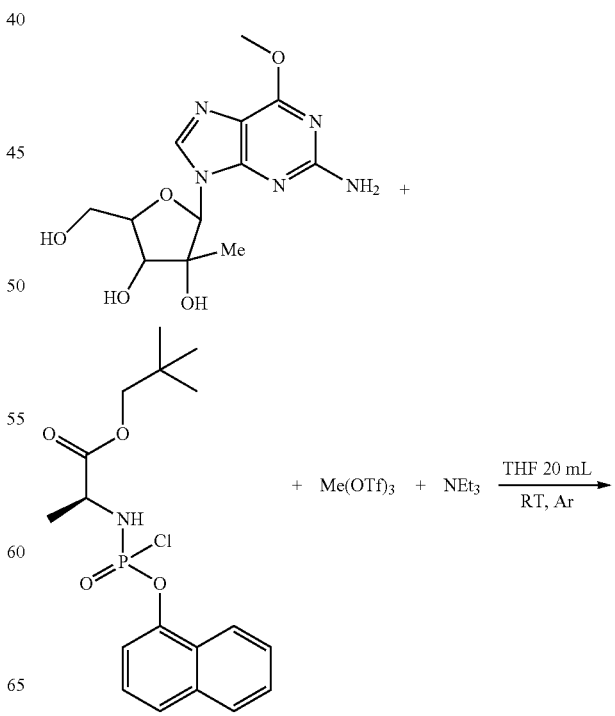

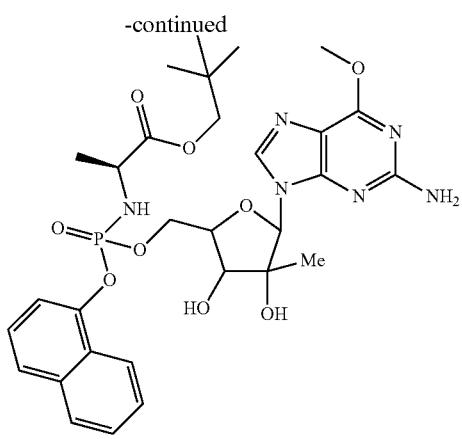

The results in terms of the ratio $R_P:S_P$ of enantiomers achieved and the yield achieved are set out in Table 4 below.

TABLE 4

Screening of other metal triflates; *the isomers ratio of $R_p:S_p$ was slightly reversed (results of two runs).

| Example | Me(OTf)₂ (equiv.) | Isomer Ratio | (% yield) |
|---|---|---|---|
| 15 | Ag(OTf) 1 equiv. | / | No reaction |
| 16 | Yb(OTf)₃ (0.1) | 1:2 | 22% |
| 17 | Fe(OTf)₃ (0.1) | 1:2 | 13% |
| 18 | La(OTf)₃ (0.1)* | 1.1:1 | 19% |

In addition, $TiCl_4$ as well as $B(C_6F_5)$ were also tested as catalyst. With titanium tetrachloride no diastereoselectivity was observed (1:1 ratio between the two isomers in 11% yield), meanwhile with tris(pentafluorophenyl)boron no reaction was observed.

Examples 19 to 22

Using the experimental procedure set out above, 2'CMe6OMeG as the nucleoside, naphthyl (onepentyl-L-alaninyl) phosphorochloridate as the phosphorochloridate and the following experimental conditions Nucleoside: 100 mg, 1 equivalent; Cu(OTf)₂ 0.1 equivalents; phosphorochloridate 1 equivalent; base 1.5 equivalents; THF 20 mL, Room Temperature, 12 hours, different bases were screened. The bases used and the results achieved in terms of $R_P:S_P$ ratio of enantiomers and yield achieved are set out in Table 5 below. Example 22 uses DMAP, which is 4-dimethylaminopyrimidine, as the base, and is a reference example.

TABLE 5

| | Variation of base | | |
|---|---|---|---|
| Example | Cu(OTf)₂ (Equiv.) | Base (1.5 equiv.) | Ratio (yield) |
| 19 | 0.1 | DIPEA | 1:2.5 (47%) |
| 20 | 0.1 | (i-pr)₂NH | 1:2.9 (42%) |
| 21 | 0.1 | DBU | B. 1:3.3 (5%) |
| 22 | 0.1 | DMAP | Traces (1:2.5) |

Examples 23 to 28

Solvent Screening

Following the experimental procedure above and using 2'CMe6OMeG as the nucleoside and naphthyl(onepentyl-L-alaninyl)phosphorochloridate as the phosphorochloridate and the following experimental conditions: Nucleoside: 100 mg, 1 equivalent; Cu(OTf)₂ 0.1 equivalents; Phosphorochloridate 1 equivalent; NEt₃ 1.5 equivalents; solvent 20 mL, Room Temperature, 12 hours, varying solvent media for use in step (i) to dissolve the nucleoside compound and the metal salt catalyst were investigated. The results in terms of the ratio $R_P:S_P$ of enantiomers and the yield achieved are set out in Table 6 below. Examples 24, 25, 27 and 28 are reference examples. "DCM" stands for dichloromethane ($CH_2Cl_2$).

TABLE 6

| | | Solvent screening | |
|---|---|---|---|
| Example | Cu(OTf)₂ (Equiv.) | Solvent (20 mL) | Ratio (Yield) |
| 23 | 0.1 | DME | 1:5 (14%) |
| 24 | 0.1 | DCM | Trace |
| 25 | 0.1 | Ethylene glycol | No reaction |
| 26 | 0.1 | 1,4 dioxane | 1:2.5 (38%) |
| 27 | 0.1 | Toluene | 1:1.5 (traces) |
| 28 | 0.1 | Pyridine | No Reaction |

Examples 29 to 35

Using the experimental procedure set out above, gemcitabine (100 mg) was employed as the nucleoside and naphthyl(isopropyl-L-alaninyl)phosphorochloridate (1 molar equiv) was employed as the phosphorochloridate. For each example, the catalyst (MX), base and solvent were employed, as set out in the reaction scheme and in Table 7 below. Example 29 employed 10 ml THF and 2 ml MeCN. Table 7 gives, for each example, the total yield and the ratio of $R_P:S_P$ enantiomers achieved. Example 31, employing Ti(OiPr)₄ as the catalyst, is a reference example. In Table 7, AA indicates the amino acid moiety corresponding to —CNHCR₁R₂CO₂—.

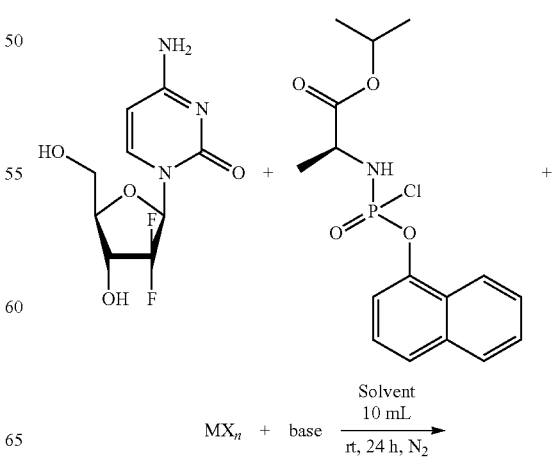

-continued

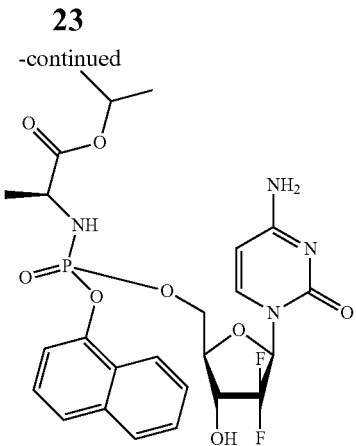

TABLE 7

Gemcitabine as the nucleoside

| Ex. | AA OR$_3$ | MX (eq.) | Base 1.5 eq. | Solvent | Yield (%) | Ratio R$_P$:S$_P$ |
|---|---|---|---|---|---|---|
| 29 | L-Ala iPr | Cu(I)OAc (0.2) | NEt$_3$ | THF/2 mL MeCN | 10 | 1:5 |
| 30 | L-Ala iPr | Cu(I)OAc (0.2) | NEt$_3$ | MeCN | 4-5 | 1:2.8 |
| 31 | L-Ala iPr | Ti(OiPr)$_4$ | NEt$_3$ | MECN | 2 | 1:3.5 |
| 32 | L-Ala iPr | Cu(I)OAc (0.2) | NEt$_3$ | THF/MeCN 1:1 | 10 | 1:4.1 |
| 33 | L-Ala iPr | Cu(I)OAc (0.6) | NEt$_3$ | DME | 10 | 1:5.2 |
| 34 | L-Ala iPr | Cu(I)OAc (0.2) | DIPEA | THF/MeCN 10 mL/2 mL | 12 | 1:8.4 |
| 35 | L-Ala iPr | Cu(I)OAc (0.5) | NEt$_3$ | THF | 4 | 1:5.3 |

Examples 36 to 42

Using the experimental procedure set out above, 2'deoxy-2'fluorouridine (100 mg) was employed as the nucleoside and naphthyl(iso-propyl-L-alaninyl)phosphorochloridate (1 molar equiv) was employed as the phosphorochloridate. The catalyst, base and solvent for each example are set out in Table 8 below. In each case, the reaction took place at room temperature under nitrogen and for 24 hours. Examples 38 and 41 are reference examples.

TABLE 8

2'deoxy-2' fluorouridine as the nucleoside

| Example | M(X)$_n$ (eq.) | Base (1.5 eq.) | solvent 10 mL | Isomer ratio (yield %) |
|---|---|---|---|---|
| 36 | CuSO$_4$ (1) | NEt$_3$ | THF | 1:3 (50%) |
| 37 | CuSO$_4$ (1) | NEt$_3$ | THF | 1:2.6 (50%) |
| 38 | CuSO$_4$ (1) | Ag$_2$CO$_3$ | THF | / |
| 39 | Cu(MeCN)$_4$•CF$_3$SO$_3$ (0.5) | DIPEA | DME | 1:2.3 (56%) |
| 40 | Cu(OTf)•C$_6$H$_6$ (0.5) | DIPEA | DME | 1:2.1 (34%) |
| 41 | Ti(OiPr)$_4$ | DIPEA | DME | |
| 42 | Cu(I)OAc (0.5) | DIPEA | DME | 1:5.6 (36%) |

Figure 2:
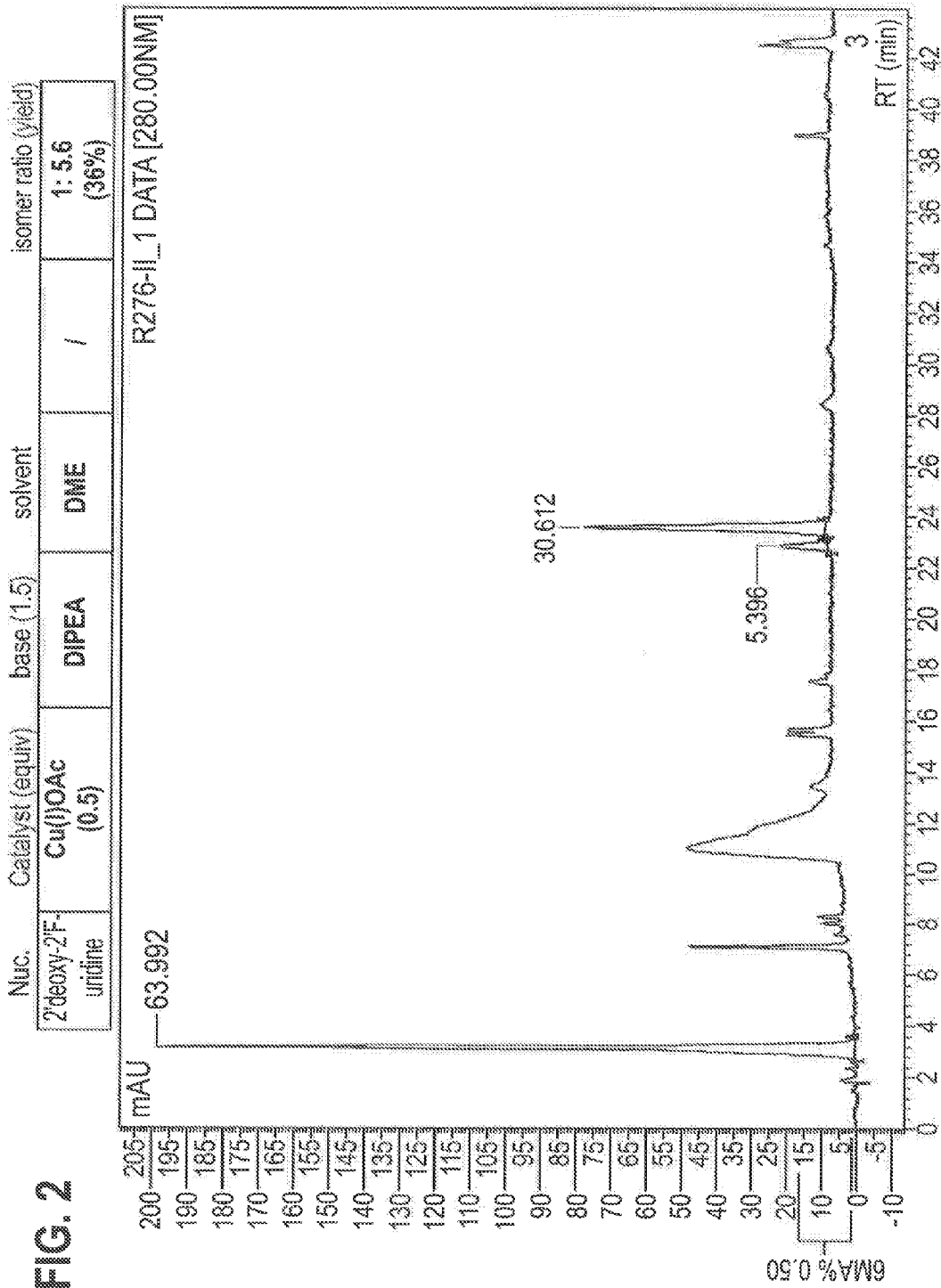
FIG. 2 shows the HPLC spectrum of the product of Example 42.

The HPLC spectrum for the product of Example 42 is shown in FIG. 2.

Example 43

Using the experimental procedure set out above, nelarabine was employed as the nucleoside (100 mg) and naphthyl (oneopentyl-L-alaninyl)phosphorochloridate (1 molar equiv) was employed as the phosphorochloridate. Cu(OTf)$_2$ (0.1 equiv) was employed as the catalyst. NEt$_3$ (1.5 equiv) was employed as the base and 10 ml of THF were employed as the solvent. The reaction took place at room temperature under argon for 12 hours.

The phosphoramidated nelarabine reaction product was produced in a yield of 80% and comprised a ratio of R$_P$:S$_P$ enantiomers of 3.6:1.

Figure 3:
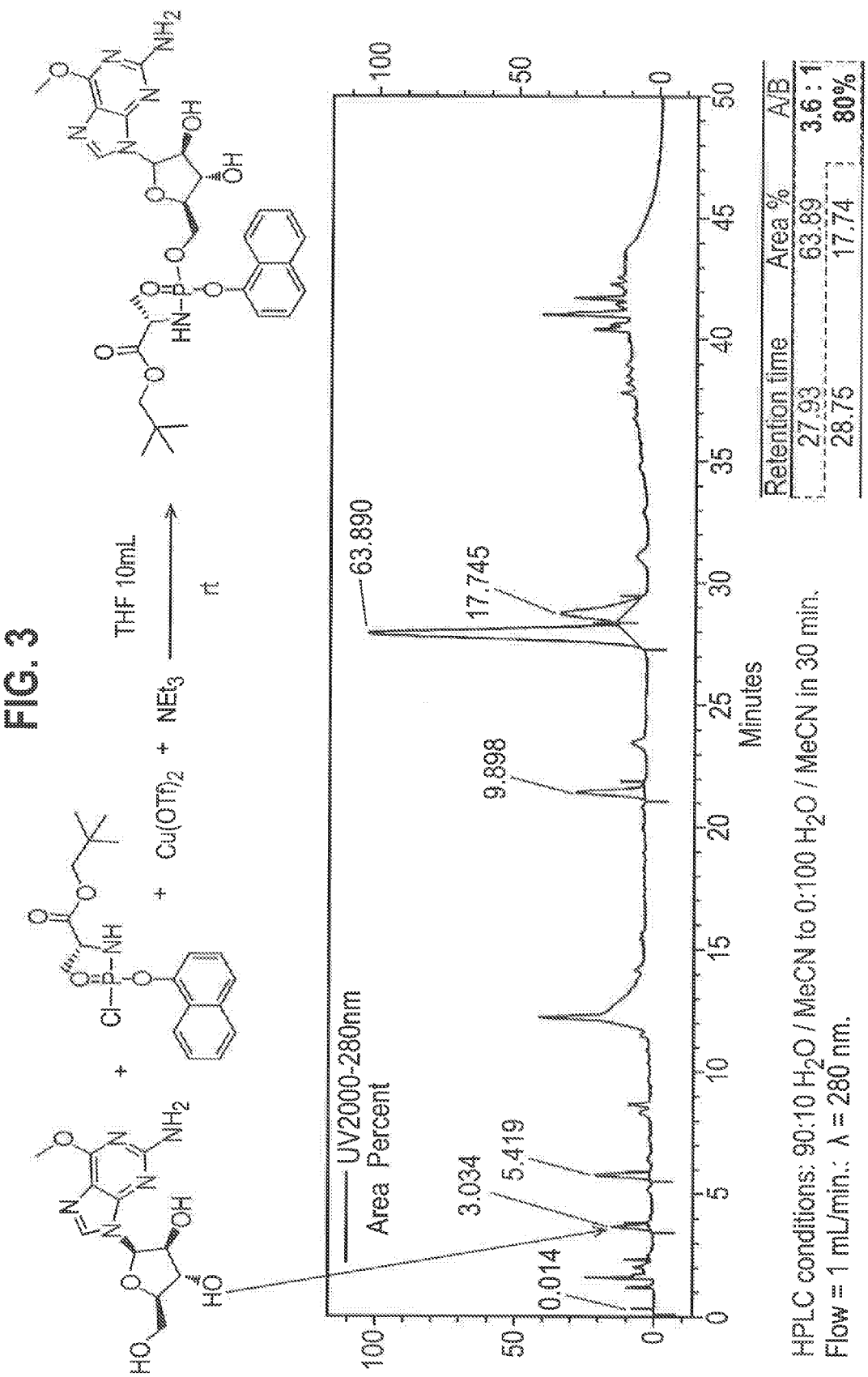
FIG. 3 shows the reaction scheme and HPLC spectrum of the product of Example 43.

The reaction scheme for the diastereoselective synthesis of protide via metal catalysis with respect to nelarabine of the present example and the HPLC of the reaction product are set out in FIG. 3. A/B in FIG. 3 refers to R$_P$/S$_P$.

Example 44

Using the above experimental procedure, clofarabine (100 mg) was employed as the nucleoside and naphthyl(oneopentyl-L-alaninyl)phosphorochloridate (1 molar equiv) was employed as the phosphorochloridate. Cu(OTf)$_2$ (0.1 equiv) was employed as the catalyst. NEt$_3$ (1.5 equiv) was employed as the base and 10 ml of THF were employed as the solvent. The reaction took place at room temperature under argon for 12 hours.

The phosphoramidated clofarabine reaction product was achieved in a yield of about 40% and comprised a ratio of R$_P$:S$_P$ enantiomers of 1:1.5.

Figure 4:
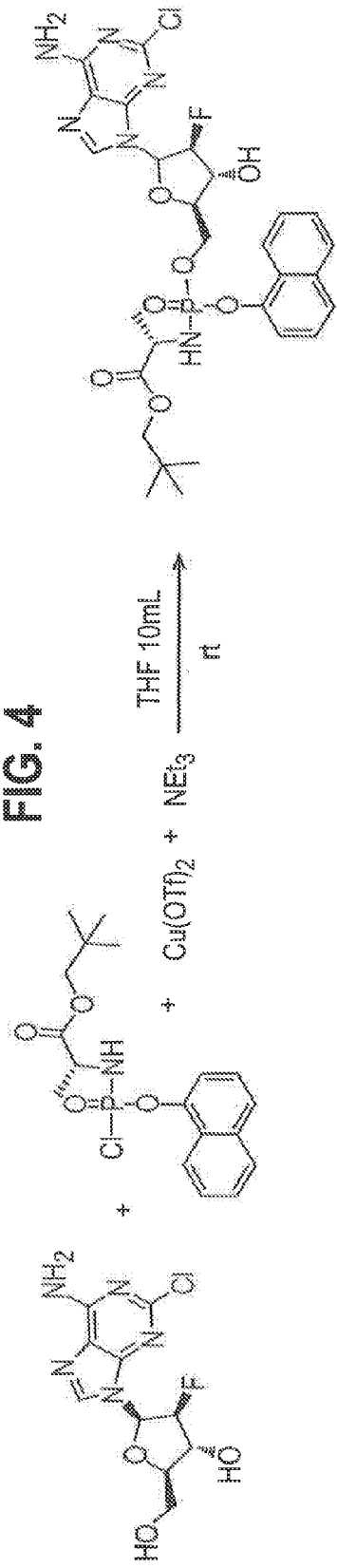
FIG. 4 shows the reaction scheme and HPLC spectrum of the product of Example 44.
Figure 4:
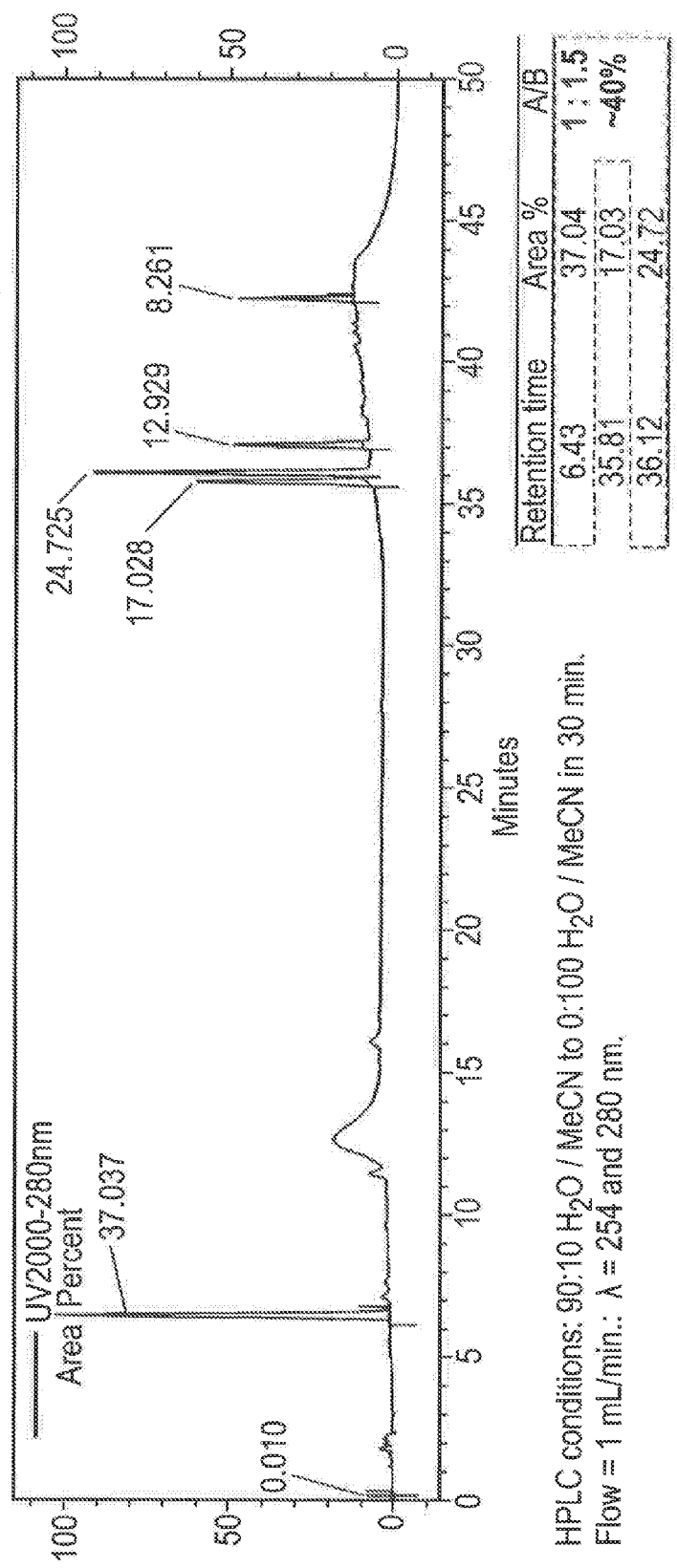

The reaction scheme for the diastereoselective synthesis of protide via metal catalysis with respect to clofarabine of the present example and the HPLC spectrum of the reaction product are set out in FIG. 4. A/B in FIG. 4 refers to R$_P$/S$_P$.

Example 45

Using the experimental procedure set out above, 2'deoxy-2'fluorouridine (100 mg) was employed as the nucleoside and naphthyl(iso-propyl-L-alaninyl)phosphochloridate (1 molar equiv.) was employed as the phosphorochloridate. 0.2 molar equivalents of Cu(OC(O)CF$_3$)$_2$ were used as the catalyst. 1.5 molar equivalents of NEt$_3$ were employed as the base. 10 ml of DME were employed as the solvent. The reaction took place at room temperature under nitrogen for 12 hours.

The phosphoramidated 2'deoxy-2'fluorouridine reaction product was produced in a yield of 35% and comprised a ratio of R$_P$:S$_P$ enantiomers of 1:5.3.

Figure 5:
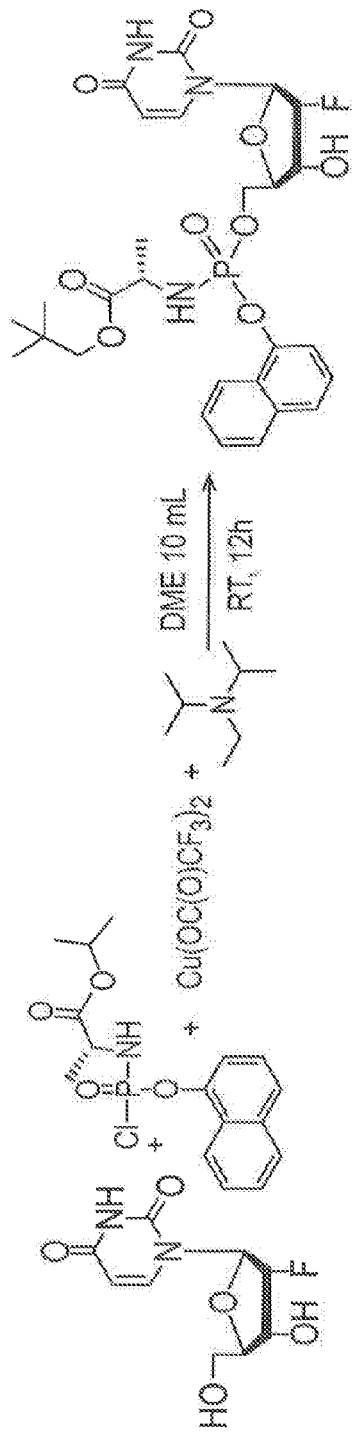
FIG. 5 shows the reaction scheme and HPLC spectrum of the product of Example 45.
Figure 5:
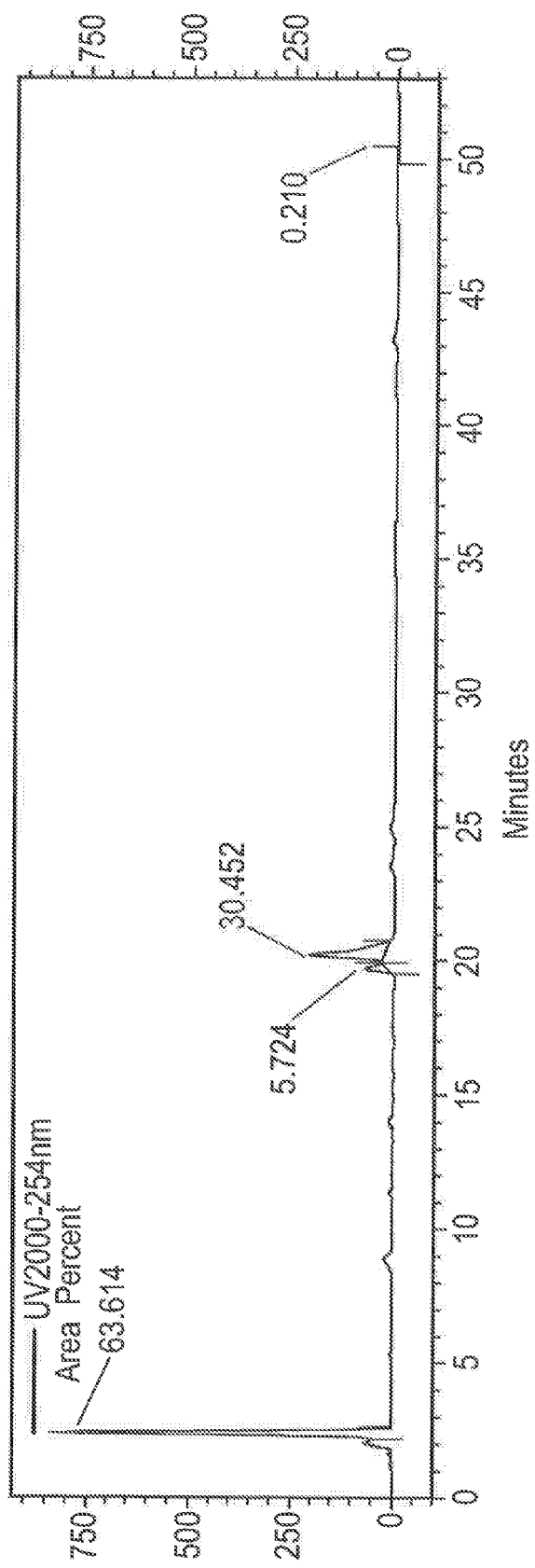

The reaction scheme of the present example and the HPLC spectrum of the reaction product are set out in FIG. 5.

Example 46

Using the experimental procedure set out above, Boc gemcitabine (100 mg) was employed as the nucleoside and naphthyl(iso-propyl-L-alaninyl)phosphorochloridate (1 molar equiv.) was employed as phosphorochloridate. 0.2 molar equivalents of Cu(OC)(O)CF$_3$)$_2$ were used as the catalyst. NEt₃ (1.5 equiv) were employed as the base. 50 ml DME were employed as the solvent. The reaction took place under nitrogen at room temperature for 24 hours.

The phosphoramidated gemcitabine reaction product was produced in a yield of 9% and comprised a ratio of $R_P:S_P$ enantiomers of 1:9.

Figure 6:
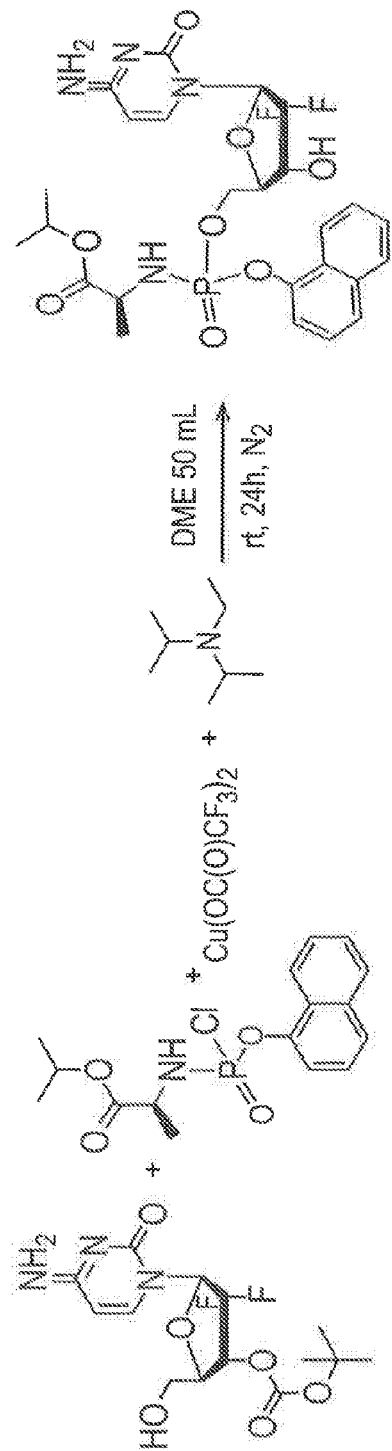
FIG. 6 shows the reaction scheme and HPLC spectrum of the product of Example 46.
Figure 6:
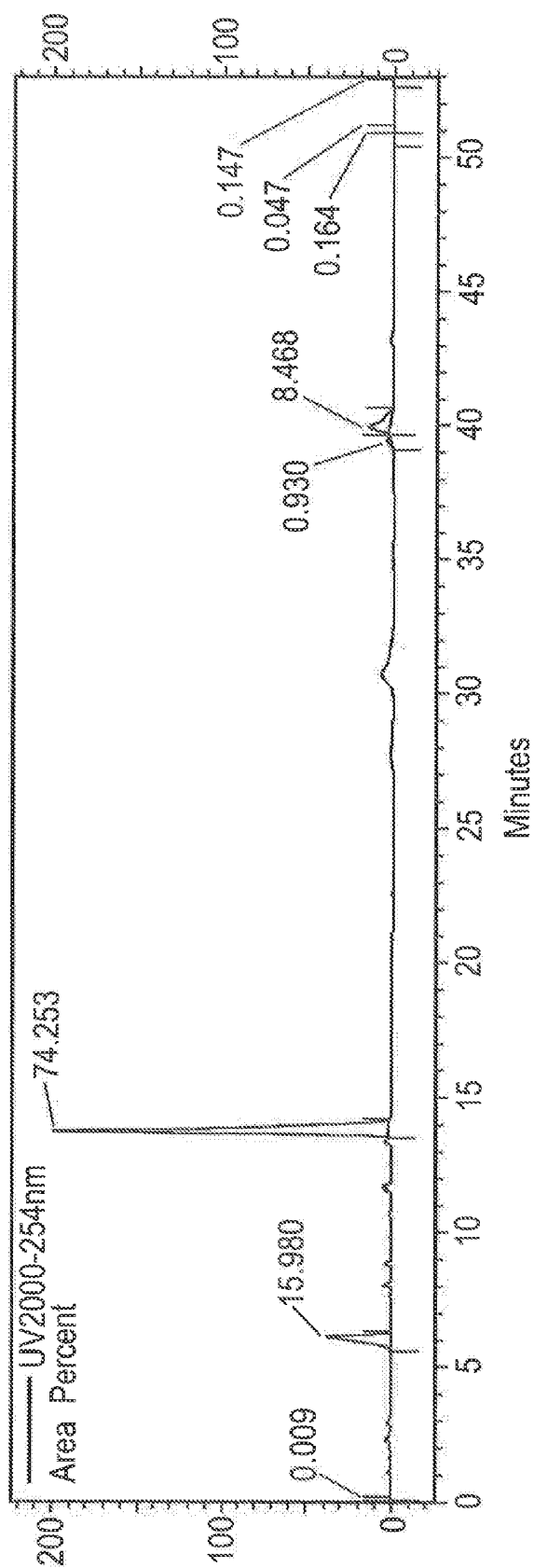

The reaction scheme of the present example and the HPLC spectrum of the reaction product are set out in FIG. 6.

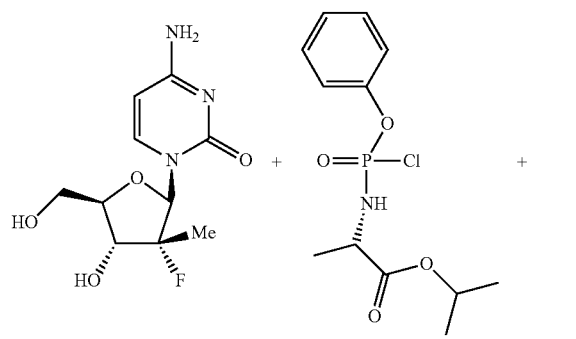

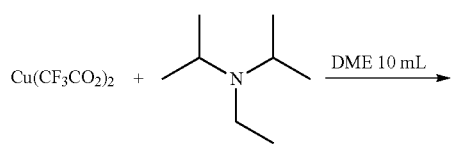

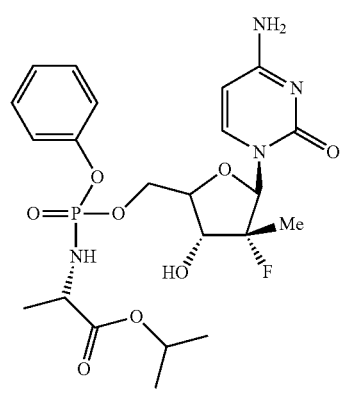

Example 47

Using the experimental procedure set out above, 4-amino-1-((2R,3R,4R5R)-3-fluoro-4-hydroxy-5-(hydroxymethyl)-3-methyltetrahydrofuran-2-yl)pyrimidin-2(1H)-one (100 mg) was employed as the nucleoside and 2 molar equivalents of phenyl(isopropyl-L-alaninyl)phosphorochloridate (150 mg) were employed as the phosphorochloridate. 0.5 molar equivalents of Cu(CF₃CO₂)₂ (30 mg) were employed as the catalyst. 1.5 molar equivalents of DIPEA (55 microliters) were employed as the base and 10 ml of DME were employed as the solvent. The reaction took place at room temperature for 24 hours.

The reaction scheme of the present example is set out below.

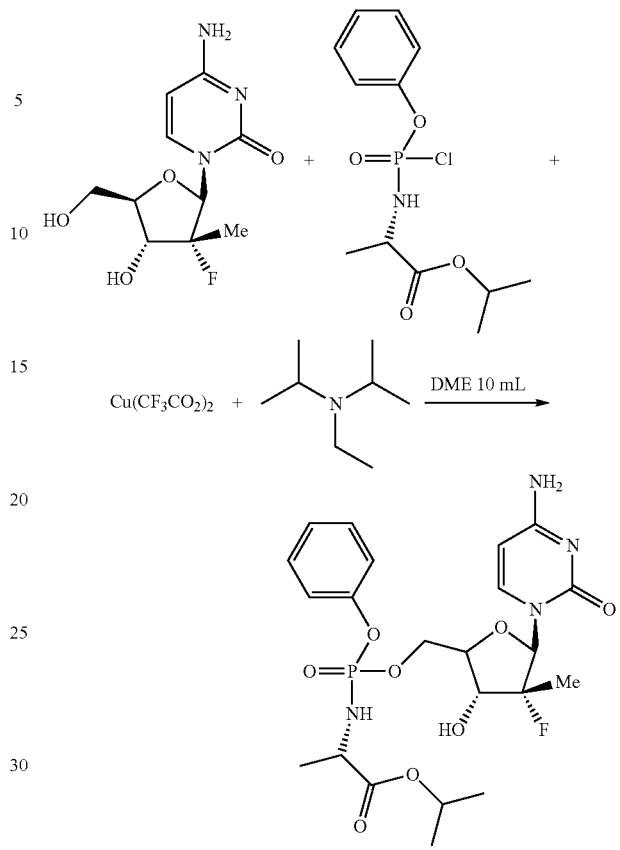

The phosphoramidated reaction product was produced in a yield of 20% and comprised a ratio of $R_P:S_P$ enantiomers of 1:66.

Figure 7:
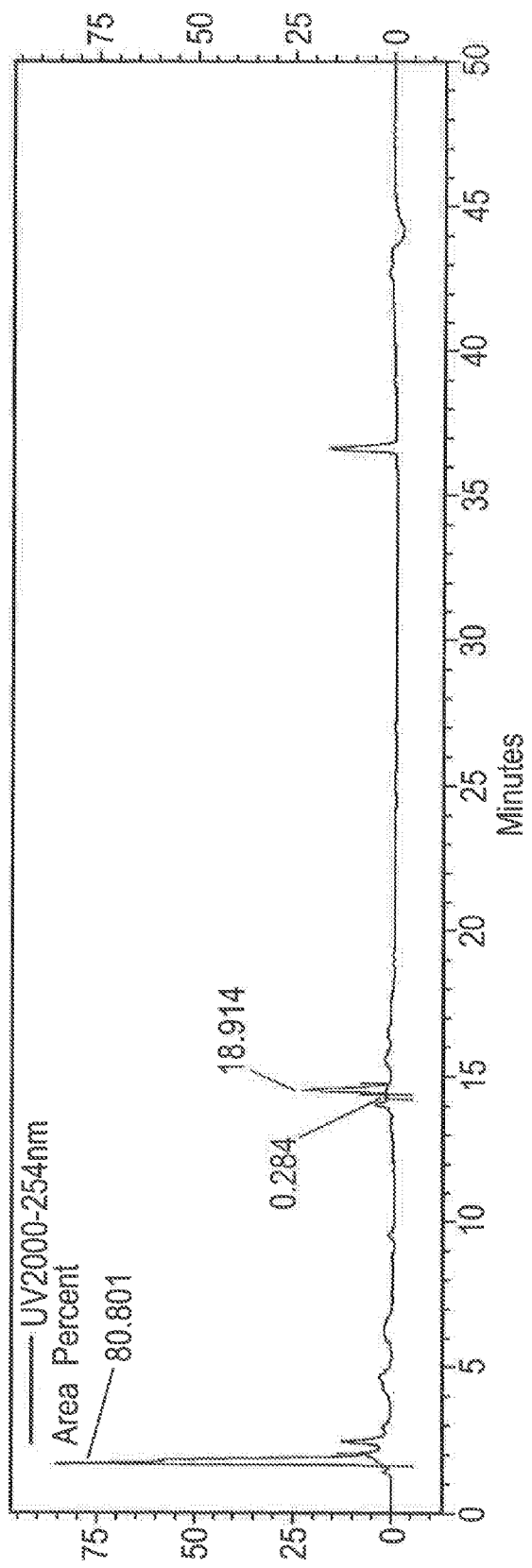
FIG. 7 shows the HPLC spectrum of the product of Example 47.

The HPLC of the phosphoramidated reaction product is set out in FIG. 7.

Example 48

Using the experimental procedure set out above, 3'-boc gemcitabine (100 mg) was employed as the nucleoside and 2 molar equivalents of phenyl(benzyl-L-alaninyl)phosphoramidate (150 mg) were employed as the phosphorochloridate. 0.5 molar equivalents of tris(acetylacetonato)FeIII (56 mg) were employed as the catalyst. 1.5 molar equivalents of DIPEA (55 microliters) were employed as the base and 10 ml of THF were employed as the solvent. The reaction took place at room temperature under nitrogen for 24 hours.

The reaction scheme of the present example is set out below.

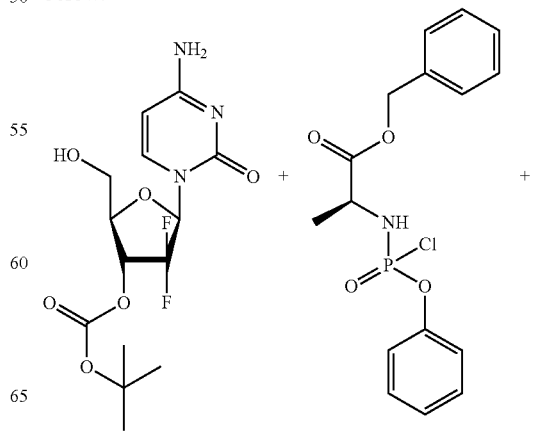

-continued

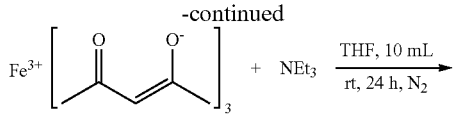

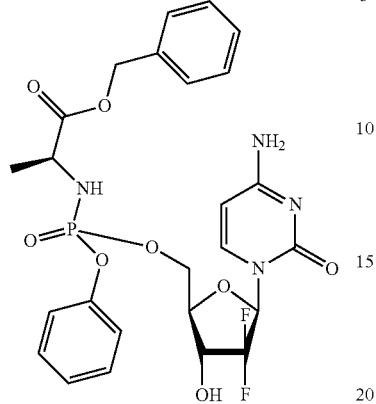

The phosphoramidated reaction product was produced in yield of 45% and comprised a ratio of $R_P$:$S_P$ enantiomers of 3:1.

Figure 8:
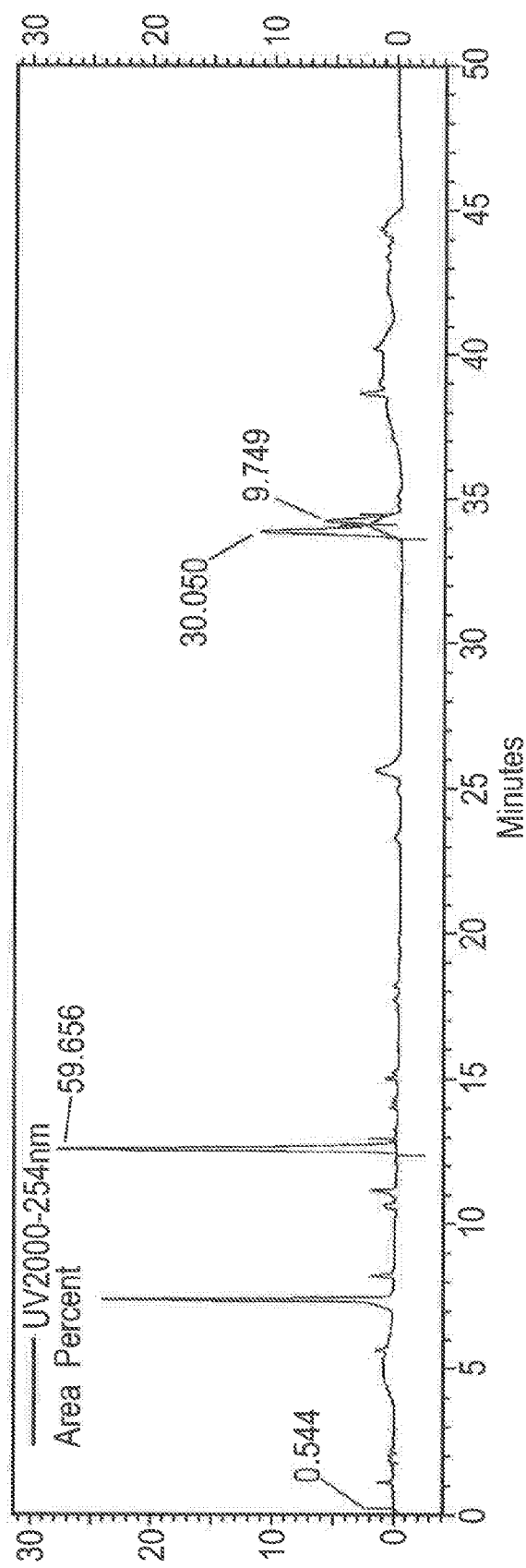
FIG. 8 shows the HPLC spectrum of the product of Example 48.

The HPLC of the phosphoramidated reaction product is set out in FIG. 8.

The invention claimed is:

1. A compound represented by:

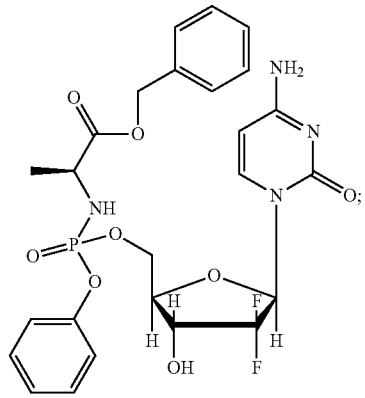

wherein the ratio of the $R_P$ diastereomer to the $S_P$ diastereomer is at most 1:20.

2. The compound of claim 1, wherein the ratio of the $R_P$ diastereomer to the $S_P$ diastereomer is 0:100.

* * * * *